United States Patent
Kaufman

(10) Patent No.: US 10,596,124 B2
(45) Date of Patent: *Mar. 24, 2020

(54) LIPID NANOPARTICLE COMPOSITIONS AND METHODS AS CARRIERS OF CANNABINOIDS IN STANDARDIZED PRECISION-METERED DOSAGE FORMS

(71) Applicant: NanoSphere Health Sciences, LLC, Greenwood Village, CO (US)

(72) Inventor: Richard Clark Kaufman, Santa Monica, CA (US)

(73) Assignee: NANOSPHERE HEALTH SCIENCES, LLC, Greenwood Village, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/015,179

(22) Filed: Jun. 21, 2018

(65) Prior Publication Data

US 2018/0296493 A1    Oct. 18, 2018

Related U.S. Application Data

(63) Continuation of application No. 15/103,850, filed as application No. PCT/US2015/034153 on Jun. 4, 2015, now Pat. No. 10,028,919.

(60) Provisional application No. 62/130,775, filed on Mar. 10, 2015.

(51) Int. Cl.
| | | |
|---|---|---|
| *A61K 9/51* | (2006.01) | |
| *A61K 31/352* | (2006.01) | |
| *A61K 9/00* | (2006.01) | |
| *A61K 47/36* | (2006.01) | |
| *A61K 9/12* | (2006.01) | |
| *A61K 9/06* | (2006.01) | |
| *A61K 31/047* | (2006.01) | |
| *A61K 36/185* | (2006.01) | |

(52) U.S. Cl.
CPC ............ *A61K 9/5123* (2013.01); *A61K 9/006* (2013.01); *A61K 9/0014* (2013.01); *A61K 9/0043* (2013.01); *A61K 9/0053* (2013.01); *A61K 9/06* (2013.01); *A61K 9/12* (2013.01); *A61K 31/047* (2013.01); *A61K 31/352* (2013.01); *A61K 36/185* (2013.01); *A61K 47/36* (2013.01)

(58) Field of Classification Search
None
See application file for complete search history.

(56) References Cited

U.S. PATENT DOCUMENTS

| | | |
|---|---|---|
| 5,662,932 A | 9/1997 | Amselem et al. |
| 5,716,637 A | 2/1998 | Anselem et al. |
| 9,925,149 B2 | 3/2018 | Kaufman |
| 10,028,919 B2 | 7/2018 | Kaufman |
| 2003/0096000 A1 | 5/2003 | Solis et al. |
| 2005/0266067 A1 | 12/2005 | Sengupta et al. |
| 2007/0072939 A1 | 3/2007 | Kupper |
| 2008/0113031 A1 | 5/2008 | Moodley et al. |
| 2008/0311214 A1 | 12/2008 | Rao |
| 2009/0074824 A1 | 3/2009 | Vila Pena et al. |
| 2011/0071118 A1 | 3/2011 | Lichtenberger |
| 2012/0093931 A9 | 4/2012 | McGinnis et al. |
| 2012/0321670 A1 | 12/2012 | Doshi et al. |
| 2013/0011484 A1 | 1/2013 | Bevier |
| 2013/0089600 A1 | 4/2013 | Winnicki |
| 2013/0095032 A1 | 4/2013 | Margalit et al. |
| 2014/0348926 A1 | 11/2014 | Hoffman et al. |
| 2016/0263047 A1 | 9/2016 | Kaufman |
| 2017/0000744 A1 | 1/2017 | Kaufman |
| 2018/0055782 A1 | 3/2018 | Kaufman |

FOREIGN PATENT DOCUMENTS

| | | |
|---|---|---|
| EP | 3057604 | 8/2016 |
| EP | 3268043 | 1/2018 |
| WO | 1993/05768 | 4/1993 |
| WO | WO 2001/049268 | 7/2001 |
| WO | WO 2008/010788 | 1/2008 |
| WO | WO 2010/008762 | 1/2010 |
| WO | WO 2012/066334 A1 | 5/2012 |
| WO | WO 2012/003003 A2 | 10/2012 |
| WO | WO 2013/105101 A1 | 7/2013 |
| WO | 2015/057751 | 4/2015 |
| WO | WO 2015/057751 A1 | 4/2015 |
| WO | WO 2016/100228 | 6/2016 |
| WO | WO 2016/144376 | 9/2016 |

OTHER PUBLICATIONS

"Cannabinoids delivery systems based on supramolecular inclusion complexes and polymeric nanocapsules for treatment of neuropathic pain." Human health and pathology, Jan. 23, 2014, abstract, online at https://tel.archives-ouvertes.fr/tel-00935588.

International Search Report for PCT/US15/34153, dated Aug. 21, 2015, 289 pgs.

Kaufman, Nanosphere Delivery Systems, Life Enhancement Products, Aug. 2013 [retrieved on Feb. 4, 2016], pp. 1-8, Retrieved from the internet: URL: http://www.life-enhancement.com/magazine/article/2910-nanosphere-delivery-systems.

(Continued)

Primary Examiner — Robert A Wax
Assistant Examiner — Randeep Singh
(74) Attorney, Agent, or Firm — Adsero IP

(57) ABSTRACT

This disclosure teaches phospholipid nanoparticle compositions of cannabinoids formed from phospholipids and simpler lipids in an unfired sequential process that encapsulate a high concentration of cannabinoids, and create standardized precision-metered dosage forms of cannabinoids; yielding an increase cannabinoid transport across hydrophobic mucosa; increase the bioavailability of the cannabinoid 2-fold to 8-fold, decrease the dose of cannabinoids 2-fold to 8-fold less than an amount of cannabinoids needed to illicit the same therapeutic effect compared to raw and non-encapsulated cannabinoids; where the nanoparticle dynamic structure reduces the adverse effects of cannabinoids; and enable safe more efficacious cannabinoid therapy.

13 Claims, 2 Drawing Sheets

(56) References Cited

OTHER PUBLICATIONS

Kaufman, Nanosphere delivery systems. Methods for overcoming bioavailability limitations: Nanosphere Delivery Systems, Aug. 2013, pp. 1-8.
First Examination report issued for Australia application 2015385825, dated Mar. 15, 2018, 3 pages.
International Preliminary Report on Patentability for PCT/US2015/034153, dated Sep. 21, 2017, 6 pages.
Bondi et al., "Lipid Nanoparticles for Drug Targeting to the Brain", Methods in Enzymology, vol. 508, pp. 229-251.
English translation of WO 9305768—google translation—obtained from https://patents.google.com/patent/WO1993005768A1/en?oq=surfactant+free+sin on Jul. 26, 2018.
Mistry et al., "Nanoparticles for direct nose-tobrain delivery of drugs", International Journal of Pharmacuetics 379 (2009) 146-157.
Office Action for Application No. 2,970,917, dated Apr. 25, 2018, 4 pages.
Office Action for Application No. 2,979,184, dated Oct. 12, 2018, 4 pages.
Vyas et al., "Intranasal drug delivery for brain targetring", Curr Drug Deliv, Apr. 2005 2(2): 165-175, obtained from https://www.ncbi.nlm.nih.gov/pubmed/16305417 on Jul. 26, 2018. Abstract.

LIPID NANOPARTICLE COMPOSITIONS AND METHODS AS CARRIERS OF CANNABINOIDS IN STANDARDIZED PRECISION-METERED DOSAGE FORMS

CROSS-REFERENCE TO RELATED APPLICATIONS

This application is a continuation of U.S. application Ser. No. 15/103,850, filed Jun. 10, 2016, entitled "Lipid Nanoparticle Compositions and Methods as Carriers of Cannabinoids in Standardized Precision-Metered Dosage Forms", which application is a 35 U.S.C. § 371 national phase application of PCT/US2015/034153 (WO 2016/144376) filed on Jun. 4, 2015, entitled "Lipid Nanoparticle Compositions and Methods as Carriers of Cannabinoids in Standardized Precision-Metered Dosage Forms", which application claims the priority benefit of U.S. Provisional Application No. 62/130,775, filed Mar. 10, 2015, and entitled "Lipid Nanoparticle Compositions and Methods as Carriers of Cannabinoids", which is incorporated herein by reference in its entirety. The entire disclosures of which are hereby incorporated by reference. Any disclaimer that may have occurred during the prosecution of the above-referenced applications is hereby expressly rescinded, and reconsideration of all relevant art is respectfully requested.

TECHNICAL FIELD

This disclosure teaches phospholipid nanoparticle compositions of cannabinoids formed from phospholipids and simpler lipids in an unfired sequential process that encapsulate a high concentration of cannabinoids, and create standardized precision-metered dosage forms of cannabinoids; yielding an increase cannabinoid transport across hydrophobic mucosa; increase the bioavailability of the cannabinoid 2-fold to 8-fold, decrease the dose of cannabinoids 2-fold to 8-fold less than an amount of cannabinoids needed to illicit the same therapeutic effect compared to raw and non-encapsulated cannabinoids; where the nanoparticle dynamic structure reduces the adverse effects of cannabinoids; and enable safe more efficacious cannabinoid therapy.

BACKGROUND

Cannabis contains more than 460 compounds of which around 70 are considered as phytocannabinoids. Hempseed oil also contains the phytcannabinoid cannabidiol (CBD). Cannabis-based medications have been intensely studied since the endogenous cannabinoid system was discovered two decades ago. Cannabis-based medications exert their effects mainly through the activation of cannabinoid receptors CB1 and CB2. Cannabinoids produce numerous therapeutic effects. They have antispastic, analgesic, antiemetic, neuroprotective, and anti-inflammatory actions. They are an effective treatment against certain psychiatric diseases.

Emerging clinical applications for cannabinoid therapies include Alzheimer's Disease, Amyotrophic Lateral Sclerosis (ALS), atherosclerosis, chronic pain, Diabetes mellitus, dystonia, epilepsy, fibromyalgia, gastrointestinal disorders, gliomas, cancer, Hepatitis C, Human Immunodeficiency Virus (HIV), Huntington Disease hypertension, incontinence, methicillin-resistant Staphyloccus aureus (MRSA), multiple sclerosis, osteoporosis, post-traumatic stress disorders (PTSD), pruritus, rheumatoid arthritis, sleep apnea and Tourette Syndrome.

One of the primary adverse effects of cannabinoid therapies in humans is disruption of short-term memory. That is consistent with the abundance of CB1 receptors in the hippocampus, the brain region most closely associated with memory. Cannabinoids impinge on the central nervous system by attaching to brain's neurons and interfering with normal communication between the neurons. These nerves respond by altering their initial behavior.

The most psychoactive phytocannabinoid in cannabis, Delta-9-Tetrahydrocannabinol 1 (THC), alters the way information is processed by the hippocampus, the part of the brain that is important for memory, learning, and the integration of sensory experiences with emotions and motivation. The hippocampus converts information into short-term memory. THC acts on the hippocampus and inhibits memory retrieval and how sensory information is interpreted. When THC attaches to CB1 receptors in the hippocampus, it weakens the short-term memory and creates structural changes to the hippocampus region of the brain. With high dosages, new information does not register into the brain and this may be lost from memory and they are not able to retrieve new information for more than a few minutes. Cannabinoid induced memory defects may, in part, be due to a reduction in acetylcholine release causing cholinergic hypofunction. THC reduces both extracellular and intracellular hippocampal acetylcholine concentrations.

The phytocannabinoid THC in cannabis may impair cognitive functions on a number of levels—from basic motor coordination to complex executive function tasks, such as the ability to plan, organize, solve problems, make decisions, remember, and control emotions and behavior. Acute exposure impairs inhibition, promotes impulsivity and impairs working memory. Residual deficit effects over a period of abstinence are most evident in tasks that require concept formation, planning and sequencing abilities. Emotional impairments are attributed to the way canabinoids affects the brain's limbic system.

The phytocannabinoids in cannabis may produce adverse cardiovascular effects A consistent effect from the phytocannabinoids in cannabis is increased heart rate. They can reduce the level of exercise which can be tolerated before the onset of angina. Cannabinoids produce profound coronary and cerebral vasodilatation in vivo by activation of vascular cannabinoid CB1 receptors. Their prominent, predictable effects on the heart, including increased work-load, increased plasma volume and postural hypotension that can impose threats to the individuals' hypertension, cerebrovascular disease or coronary arteriosclerosis. High doses of cannabis measured as 15 mg of THC are shown to increase heart rate, gross motor disturbances, and can lead to panic attacks.

Cannabinoids also produce a tolerance. Prolonged exposure to phyto synthetic or endogenous cannabinoid agonists is associated with the development of tolerance for most of their pharmacological effects essentially due to adaptive down-regulation and desensitization of cannabinoid receptors.

Currently employed methods of delivery of cannabis derived cannabinoids include inhalation delivery methods of smoking, vaporization and aerosols; oral ingestion delivery methods into the GI tract of infused products, edibles, extract oils, tinctures and soft gel caps; and intraoral delivery methods to the oral mucosa via sprays and drops of cannabis as tinctures, extracts, and emulsion compositions, and cannabis containing chewing gums.

Methods of delivering hempseed derived cannabinoids include oral ingestion delivery into the GI tract of infused products, edibles extract oils, tinctures and soft gel caps and intraoral delivery to the oral mucosa via sprays and drops of cannabis as tinctures, extracts, and emulsion compositions, and chewing gums.

Inhalation delivery methods of smoking and vaporization have no reliable dosage as medicine. Bioavailability following the smoking route was reported as 2-56%, due in part to intra- and inter-subject variability in smoking dynamics, which contributes to uncertainty in dose delivery. The number, duration, and spacing of puffs, hold time, and inhalation volume, or smoking topography, greatly influences the degree of exposure and blood levels.

Oral delivery methods of ingesting extracts, infusions and edibles forms have typically a delay in the onset of their actions making it extremely difficult in ingest the correct dosage of cannabinoids. The oral absorption of THC and CBD are typically reported as 6% bioavailability to the systemic circulation after extensive first pas liver metabolism. Oral delivery is slow and unpredictable, with peak concentrations occurring 1-5 hours post dose.

Several factors account for the low oral bioavailability of cannabinoid as compared to intravenous administration. They include low solubility and dissolution, variable absorption, degradation in the stomach, and significant first-pass metabolism to active and inactive metabolites in the liver. There may be variation in potency of cannabinoid constituents from crop to crop and even in the same cannabis depending upon its, age, moisture content and methods of curing. Furthermore oral ingested products often lack accurate information of the cannabinoid content per dosage and an accurate and reliable method to regulate the dosage of cannabinoids administered.

Intraoral delivery of cannabinoids to the sublingual or buccal oral mucosa delivery by spray and drops has not demonstrated significant pharmacokinetic differences from that of oral administration. Research found no statistically significant differences in bioavailability and pharmacokinetics between similar dosages of oral administered THC and the oral mucosal spray Sativex of GW Pharma delivering 2.7 mg THC and 2.5 mg cannabidiol (CBD) per actuation as demonstrated by their comparative by Cmax, time to maximum concentration or in their AUC. If THC in Sativex was primarily absorbed through the oral mucosa, bypassing first pass metabolism in place of being swallowed, one would expect a difference between oral THC and Sativex 11-OH-THC/THC ratios. Their high ratio indicates gastric degradation and extensive first-pass metabolism; however, no statistical difference was found.

This disclosure teaches methods and compositions of cannabinoids to overcome their intrinsic low oral bioavailability, reduce cannabinoid dosages without loss of therapeutic efficacy, increase suitability for long-term or daily cannabinoid therapy and reduce cannabinoids adverse effects.

The disclosure teaches methods and delivery system compositions of cannabinoids that increase the bioavailability, bioactivity, therapeutic activity and therapeutic index of cannabinoids for cannabinoid therapy.

The disclosure teaches methods and delivery system compositions of cannabinoids in standardized precision-metered dose forms that deliver the same amounts of cannabinoids in each administration, rapidly reach the systemic circulation and maintain consistent plasma levels over time; with the ability to enable precision dispensing and create a high degree of user compliance.

The disclosure teaches methods and compositions that provide enhanced cannabinoid bioactivity, increased therapeutic activity, at lower doses and with fewer adverse actions; deliver standardized precision-metered dosage forms of cannabinoids; and administration by more effective methods of delivery, making cannabinoid drug treatments more efficacious and available to a larger number of patients.

SUMMARY OF THE EMBODIMENTS

This disclosure teaches phospholipid nanoparticle compositions of cannabinoids formed from phospholipids and simpler lipids in an unified sequential process that encapsulate a high concentration of cannabinoids; yielding an increase cannabinoid transport across hydrophobic mucosa; increase the bioavailability of the cannabinoid 2-fold to 8-fold, decrease the dose of cannabinoids 2-fold to 8-fold less than an amount of cannabinoids needed to illicit the same therapeutic effect compared to raw and non-encapsulated cannabinoids; where the nanoparticle dynamic structure reduces the adverse effects of cannabinoids; and enable safe, daily, long term and more efficacious cannabinoid therapy.

The disclosure teaches the use of phospholipid nanoparticle compositions encapsulating cannabinoids enabling cannabinoids to more efficiently bind to receptors for therapeutic activity.

The disclosure teaches the use of phospholipid nanoparticle compositions encapsulating cannabinoids enabling cannabinoids to produce fewer adverse side effects during cannabinoid therapy.

This disclosure teaches encapsulating cannabinoids in phospholipid nanoparticles liquid gels enabling cannabinoids to be taken by sublingual intraoral, nasal and transdermal routes of administration and produce greater therapeutic acclivity with a higher therapeutic index compared to similar doses of the same cannabinoids taken by peroral administration.

This disclosure teaches encapsulating cannabinoids in phospholipid nanoparticles liquid gels enabling cannabinoids to be taken by sublingual intraoral, nasal and transdermal routes of administration and produce greater therapeutic acclivity with a higher therapeutic index compared to similar doses of the same cannabinoids taken by peroral administration.

This disclosure teaches encapsulating cannabinoids in phospholipid nanoparticles liquid gels compositions that deliver standardized and precision-metered dosages of cannabinoids.

This disclosure teaches methods of treatment for a patient comprising phospholipid nanoparticle carrier compositions of cannabinoid delivery.

DESCRIPTION OF THE FIGURES

FIGS. 1-4 are derived from Agurell et al., PharmRev 1986_vol. 38_21PK-MetabD1THC-22-43.

DETAILED DESCRIPTION OF THE DISCLOSURE

Figure 1:
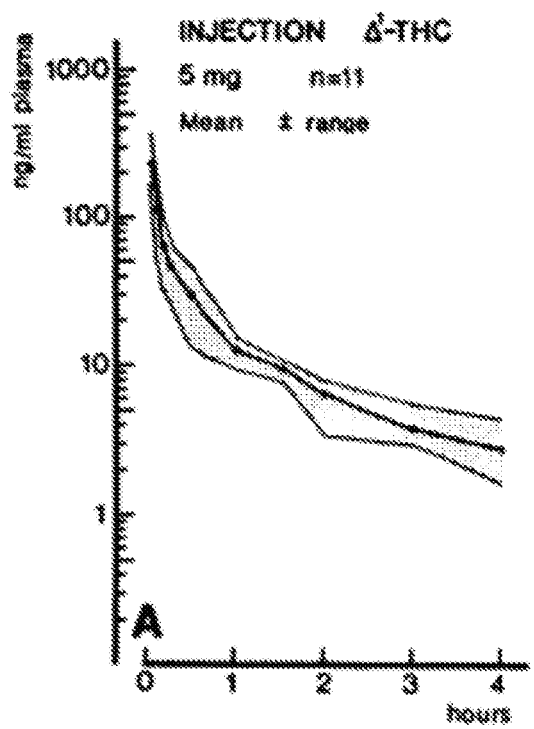
FIG. 1 shows the average plasma THC concentrations during 4 hours after administration of 5.0 mg i.v. This figure is derived from FIG. 2 from Agurell et al., PharmRev 1986_vol. 38_21PK-MetabD1THC.
Figure 2:
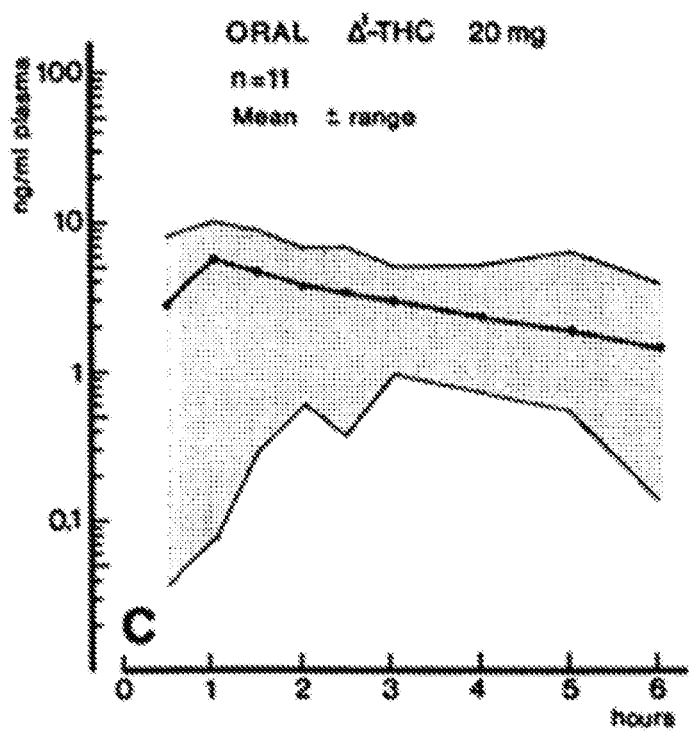
FIG. 2 is the average plasma THC concentrations during 5 hours after administration of 5.0 mg of THC in a brownie. This figure is derived from FIG. 2 from Agurell et al., PharmRev 1986_vol. 38_21PK-MetabD1THC.
Figure 3:
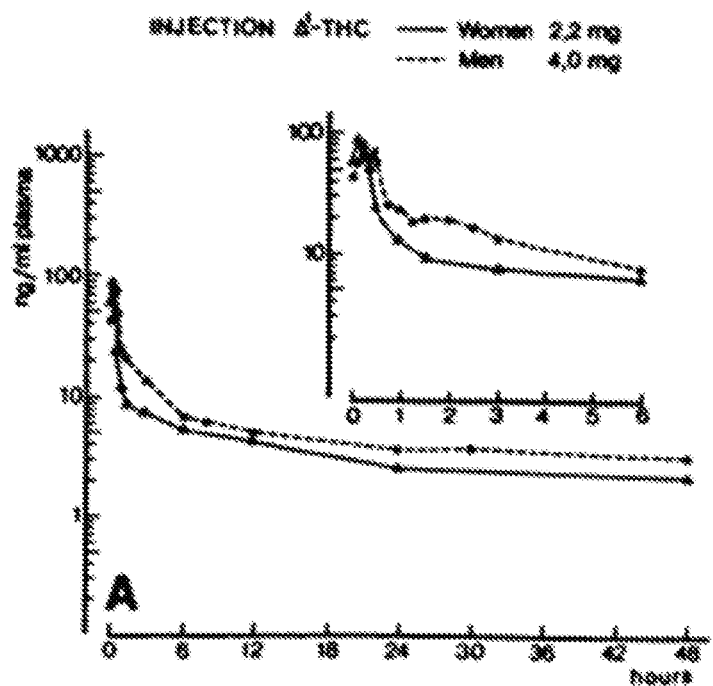
FIG. 3 is the observed plasma THC concentrations in a group of women administered 2.2 mg and men administered 4.0 mg by slow i.v. injection (20-30 min). This figure is derived from FIG. 3 from Agurell et al., PharmRev 1986_vol. 38_21PK-MetabD1THC.
Figure 4:
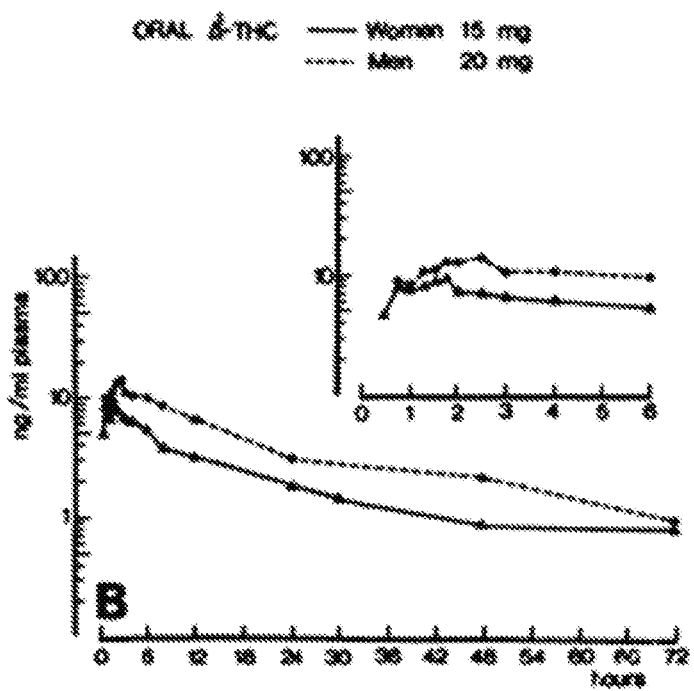
FIG. 4 is the observed plasma THC concentrations in a group of women administered 15 mg and men administered 20 mg in sesame oil by oral administration. This figure is derived from FIG. 3 from Agurell et al., PharmRev 1986_vol. 38_21PK-MetabD1THC.

Unless otherwise indicated, all numbers expressing quantities of ingredients, dimensions reaction conditions and so forth used in the specification and claims are to be understood as being modified in all instances by the term "about".

In this application and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element" or "component" encompass both elements and components comprising one unit and elements and components that comprise more than one unit unless specifically stated otherwise.

The term "phospholipid nanoparticle" in the present disclosure refers to different types of compositions of nanoscale particles as carriers containing essential phospholipids that encapsulate cannabinoids by using a molecular assembly technique to carry the cannabinoid across cell membranes and biological barriers to deliver the cannabinoid to target cell sites of the human body where they produce therapeutic activity.

The term "NanoSphere" in the present disclosure refers to phospholipid lipid nanoparticles as liquid gels that are mostly less than 100 nm diameter and typically in the range of 50 nm to 150 nm. NanoSpheres have high stability and minimal leakage of contents into the GI tract and blood. NanoSpheres possess high long-term stability. NanoSpheres readily pass across cell membranes. Nanospheres allow for high encapsulation of cannabinoids, and strong protection of ingredients. Nanospheres have a high degree of compatibility, versatility, usability and safety for cannabinoids.

The term "phospholipids" in the present disclosure refers to a triester of glycerol with two fatty acids and one phosphate ion. Phospholipids include natural occurring phospholipids like phosphatidylcholine sphingosine, gangliosides, and phytosphingosine and combinations thereof derived from soy and lecithin that are preferable for use in this disclosure and the synthetic phospholipids that include but are not limited to diacylglycerols, phosphatidic acids, phosphocholines, phosphoethanolamines, phosphoglycerols.

The term "essential phospholipids" in the present disclosure refers to the highly purified extract of characteristic fatty acid composition of the phospholipids distinguished by their particular high content of polyunsaturated fatty acids, predominantly linoleic acid (approx. 70%), linolenic acid and oleic acid and with a high content exceeding 75% of (3-sn-phosphatidyl) choline. Beside phosphatidylcholine molecules, the essential phospholipid fraction includes phosphatidylethanolamine, phosphatidylinositol and other lipids.

The term "medium chain triglyceride" (MCT) "in the present disclosure refers to a class of triglyceride oil that are probably naturally derived from fatty acids that are usually about 8 to about 12 carbons in length. Such oil is commercially available as Miglyol 812, Miglyol 810, Captex 355 and Neobees M-5.

The term "cannabinoid" in this disclosure refers to any of the diverse chemical compounds that act on cannabinoid receptors on cells in the brain, act on orthosteric or allosteric sites and modulate endocannabinoid activity. They include the phytocannabinoids found in cannabis, hempseed oil, other plants, and synthetic cannabinoids manufactured artificially. They include the phytocannabinoids delta-9-tetrahydrocannabinol (THC), cannabidiol (CBD), cannabinol (CBN) cannabigerol (CBG), cannabigerol (CBG), cannabichromene (CBC), cannabicyclol (CBL), canabivarol (CBV), tetrahydrocannabivarin (THCV), cannabidivarin (CBDV), cannabichromevarin (CBCV), cannabigerol monoethyl ether (CBGM), or the like; or mixtures or combinations thereof. Other botanical cannabimimetics include N-alkylamides from Echinacea and B-caryophyllene. They include mixtures of phytocannabinoids separated from the plant by extraction techniques and high purity cannabinoids obtained by purification from natural sources or via synthesis.

The term "bioavailability" in this disclosure refers to the physiological availability of a given amount of a drug as distinct from its chemical potency; proportion of the administered dose that is absorbed into the bloodstream.

The term "therapeutic activity" in this disclosure refers to the effect or response of a cannabinoid in the treating or curing of disease.

The term "therapeutic index" in this disclosure refers to the therapeutic window or safety window and comparison of the amount of a cannabinoid that causes the therapeutic effect to the amount that causes adverse effects.

The term "cannabinoid adverse effects" in this disclosure refers to the adverse effect of cannabinoid therapy. These problems include impaired cognition, disruption of memory, behavioral changes, emotional changes, and cardiovascular effects, including increased heart rate, increased work-load, increased plasma volume and postural hypotension and developing a tolerance to cannabinoids.

The term "cannabinoid therapy" in this disclosure refers to the use of cannabinoids to prevent, treat and/or ameliorate and disease and/or pathology that includes and is not limited to Alzheimer Disease, Amyotrophic Lateral Sclerosis (ALS), chronic pain, diabetes mellitus, dystonia, epilepsy, fibromyalgia, gastrointestinal disorders, gliomas, cancer, Hepatitis C, Human Immunodeficiency Virus (HIV) Huntington Disease, hypertension, incontinence, methicillin-resistant Staphyloccus aureus (MRSA), multiple sclerosis, osteoporosis, pruritus, rheumatoid arthritis, sleep apnea and Tourette Syndrome.

The terms "cell membranes", "biological barriers" and "mucosa barriers" in this disclosure refer to 1) the mucosal membrane barriers of the oral cavity; 2) the mucosal membrane barrier of the GI tract; 3) the dermal and epidermal cell membrane barriers; 4) the BBB; 5) the blood-ocular barrier consisting of the blood-aqueous barrier and the blood-retinal barrier; 6) ocular barriers of the conjunctiva and corneal epithelium; and 7) the mucosa of the nasal cavity 8) the cell membrane barriers of the nervous system, respiratory system, circulatory system, GI system, muscular system, urinary system, genital system, internal organs, and tissues.

The term "encapsulate" in this disclosure refers coating of various substances within another material at sizes on the nano scale. The encapsulated material is referred to as the internal phase, the core material the fill. The encapsulation material is known as the external phase, the shell, coating or membrane. In one embodiment this refers to lipid nanoparticles have an external phase (membrane) of essential phospholipids and an internal phase (core) of cannabinoids and simpler lipids or aqueous/lipid emulsions.

The term "ligand" in this disclosure refers to any material that may be bound to the surface of the nanoparticle or nanostructure for the linking of nanoparticles to form nanometer-scale geometric structures.

The term "viscoelastic" in this disclosure refers to the simultaneous existence of viscous and elastic properties of nanoparticles and their behavior thereof from intermolecular and interparticle forces in their compositional material.

The term "biocompatible" in this disclosure refers to the ability of nanoparticle compositions and biomaterials to perform their desired functions without eliciting any undesirable local or systemic effects in the recipient, generating the most appropriate beneficial cellular and tissue responses and optimizing the performance of their payloads. This is especially relevant on the nanoscale where biomaterials function differently can introduce undesirable, adverse and sometimes toxic effects.

The term "biodegradable" in this disclosure refers to the ability of nanoparticle compositions and biomaterials to rapidly metabolize in vivo and resulting metabolites that are nontoxic and readily eliminated.

The term "surfactant" in this disclosure refers to compounds that lower the surface tension (or interfacial tension) between two liquids or between a liquid and a solid act as emulsifiers, dispersants, wetting agents and viscosity modifiers. In one embodiment surfactants means amphiphilic molecules which are manufactured by chemical processes or purified from natural sources or processes that can be anionic, cationic, nonionic, and zwitterionic.

The term "cannabis concentrate" in this disclosure refers to the cannabinoids of the cannabis plant that have been extracted using one of the many known extraction methods In one embodiment cannabis concentrates refer to cannabis oil, budder, wax or shatter.

The term "cannabis extracts" in this disclosure refers to the cannabinoids of the cannabis plant that have been extracted and concentrated using one of the many known extraction methods including non-hydrocarbon solvent extracts from water, carbon dioxide and isopropyl alcohol; hydrocarbon solvent extracts from butane, propane, and hexane; and dry sieve method.

The term "ultrasonification" in this disclosure refers methods in the assembly of phospholipid nanoparticles from ultrasound waves in which ultrasonic amplitudes generate intense cavitation alternating high-pressure and low-pressure cycles that disperse and break up particles down to the nanometer scale. In one embodiment ultrasonification refers to high power ultrasonic liquid processors also known as sonicators, ultrasonic homogenizers, sonochemical reactors ultrasonic mixers and ultrasonic wet-milling systems.

The term "homogenization" in this disclosure refers to high-shear fluid processing reducing the size of droplets and particles in liquid-liquid dispersions to submicron sizes. In one embodiment homogenization refers to high shear fluid processors such as the Ultra-Turrax, Kinematika Polytron and Silverson processors used for dispersing, particle reduction and liquid mixing. In one embodiment homogenization refers high pressure homogenization piston gap and microfluidization methods such as APV Gaulin, Avestin and Microfluidics homogenizers used for making nanoparticles.

In one embodiment of this disclosure homogenization methods that include high pressure homogenization and microfluidization are the method of assembly for producing phospholipid nanoparticle carrier compositions of cannabinoids of nanoparticle with viscoelastic gels and standardized precision-metered dosage forms of cannabinoids.

The term "milling" in this disclosure refers methods in the assembly of phospholipid nanoparticles by which an external force is applied to a solid that leads to its break-up into smaller particles. In one embodiment milling refers Milling refers wet grinding carried out using methods as a roller ointment mill, tumbling ball mill, vibratory ball mill, a planetary ball mill, a centrifugal fluid mill, an agitating beads mill, a flow conduit beads mill, an annular gap beads mill, and wet jet mill. In one embodiment milling refers to dry grinding by compression or by friction, using methods as a jet mill, a hammer mill, a shearing mill, a roller mill, a shock shearing mill, a ball mill, and a tumbling mill. In one embodiment milling refers to wet processes for preventing the condensation of the nanoparticles so formed, and obtaining highly dispersed nanoparticles.

The term mammal is intended to include, but not limited to, humans in this disclosure.

Cannabinoid Therapy

Cannabinoid based medications have been intensely studied since the endogenous cannabinoid system was discovered two decades ago. Cannabis-based medications exert their effects mainly through the activation of cannabinoid receptors CB1 and CB2.

Cannabinoids produce numerous therapeutic effects. They have antispastic, analgesic, antiemetic, neuroprotective and anti-inflammatory actions. They are an effective treatment against certain psychiatric diseases. Emerging clinical applications for cannabinoid therapies include Alzheimer Disease, Amyotrophic Lateral Sclerosis (ALS), chronic pain, Diabetes Mellitus, dystonia, epilepsy, fibromyalgia, gastrointestinal disorders, gliomas/cancer, Hepatitis C, Human Immunodeficiency Virus (HIV), Huntington Disease, Hypertension, Incontinence, Methicillin-resistant Staphyloccus aureus (MRSA), Multiple Sclerosis, osteoporosis, pruritus, rheumatoid arthritis, sleep apnea and Tourette Syndrome.

Due to the chemical complexity of the cannabis plant material compared to synthetic THC, extracts of cannabis that capture the full range of phytocannabinoids are being explored as therapeutic medications. Product offerings includes Tetranabinex®, which is high in THC, and Nabidiolex®, which is high in CBD and Sativex® which contains equal amounts of THC and CBD.

Phytocannabinoids are separated from the cannabis plant by extraction techniques. Once extracted, cannabinoid blends can be separated into individual components using wiped film vacuum distillation or other distillation techniques. The relative amount of each principal phytocannabinoid in cannabis extract varies according to the cannabinoid profile and levels of the particular plants and methodology of extraction. High purity cannabinoids are obtained by purification from a natural source or via synthetic means.

Phytocannabinoids predominatly CBD are separated from hempseed by extraction techniques. The relative amount of CBD in hempseed extract varies according to CBD content of the hemp plants and methodology of extraction.

Cannabinoids produce their effects through their interaction with specific receptors. The two known types of cannabinoid receptors, called CB1 and CB2, form the basis of the Endocannabinoid System. The Endocannabinoid System regulates numerous fundamental physiological processes involving the CNS and autonomic nervous system, immune, endocrine, reproductive and cardiovascular activity. Imbalances in the Endocannabinoid System can produce impairments of various processes including neuroinflammation, immunomodulation and food control. The Endocannabinoid System has been shown to be involved in different pathologies including Alzheimer disease, Multiple Sclerosis, Parkinson disease, chronic inflammation, chronic pain, cancer, nausea, vomiting, obesity, epilepsy, glaucoma, asthma and mood disorders.

CB1 receptors are found primarily in the brain, specifically in the basal ganglia and in the limbic system, including the hippocampus. CB2 receptors are almost exclusively found in the immune system, with the greatest density in the spleen. CB2 receptors appear to be responsible for the anti-inflammatory and possible other therapeutic effects of cannabis. Cannabinoids bind reversibly and stereo-selectively to the cannabinoid receptors. The affinity of an individual cannabinoid to each receptor determines the effect of that cannabinoid. Cannabinoids that bind more selectively to certain receptors are more desirable for medical usage.

Cannabinoid receptors are what are known as G-Protein Coupled Receptors (GPCRs). These receptors are embedded in the cell membrane where they are coupled to G-proteins. The binding of the cannabinoid ligand to the receptor leads to a signaling cascade that either decreases or increases the activity of a particular enzyme to raise a receptor response above basal activity They target proteins that are usually transcription factors, proteins that bind DNA and promote the expression of certain genes within the cell that alter cellular communication.

Endogenous and exogenous cannabinoids or cannabinoid-like compounds can activate different signaling pathways engaging receptors independent of CB1 and CB2 receptors. Behavioral effects of cannabinoids may occur through other receptors or a synergic action of CB receptors with these other receptors. Other receptors for cannabinoids include the transient receptor potential vanilloid type-1 (TRPV1) receptor, the deorphanized G protein-coupled receptor GPR55, the peroxisome proliferatoractivated receptors (PPAR, the N-arachidonoyl glycine (NAGly) receptor, serotonin receptor (5-HT)3, acetylcholine receptors (nACh), the glutamate receptor (NMDA). TASK-1 channel and Na+ channel T-type Ca2+ channels.

Cannabinoids interactions with proteins transduce signals that effect the actions and efficacy of other neurotransmitters receptors. They act on specific neurotransmitters in respect to certain memory regions of the brain. Glutamate, dopamine and acetylcholine are three neurotransmitter systems that are thought to play in the adverse memory effects of cannabinoids.

In particular, recent research focuses on glutamate for its responsibility in hippocampus long-term depression (LTD)—the long-lasting decrease of synaptic excitability. Additionally, dopamine is often investigated for its possible role in working memory within the prefrontal cortex. Other research has observed decreased levels of hippocampus acetylcholine from cannabinoids producing adverse effects on behavioral tasks.

Cannabinoids Effects on Cell Membranes

Cell membranes are primarily composed of a variety of lipids in the form of two asymmetric leaflets and functional proteins. The membranes define a cellular boundary and provide a basic platform for tight regulation of many biological processes, including material transport, signal transduction, trafficking, pathogenic pathways, intercellular organization and response to the extracellular matrix.

Owing to their lipophilicity, the cannabinoids accumulate in the lipid part of cell membranes and they occupy binding sites localized on hydrophobic portions of integral membrane proteins. Furthermore, cannabinoids exhibit a slow clearance from the body. They alter the functions of various membrane proteins which participate in signal transduction, the function of the lipid part of cell membranes and the role of essential fatty acids.

Because of their high hydrophilic properties, high concentrations of cannabinoids alter cell membrane fluidity. Lipids constitute 40% to 80% of the total membrane and phospholipids accounting for a major proportion of the lipid fraction. Phosphatidylcholine is the most abundant phospholipid in the membrane accounting for 50% of its content. The fluidity or flexibility of membranes is dependent on the degree of unsaturation of the fatty acids forming the membrane. As the degree of unsaturation increases, the cell membrane becomes more flexible and fluid.

Cannabinoids are deposited on cell membranes, positioning themselves in the lipid portion, where they alter the fluidity and functional state of the membrane. It is thought that the various adverse effects associated with the chronic use of cannabinoids, including increased tolerance to cannabinoids over time, result from the interaction of cannabinoids with cell membranes.

Low Bioavailability of Oral and Intraoral Delivered Cannabinoids

Cannabinoids are nearly insoluble in water but soluble in lipids, alcohols and other non-polar organic solvents. Their poor solubility and low dissolution rate in the aqueous gastrointestinal fluids and significant first-pass liver metabolism result in low oral cannabinoid bioavailability. The bioavailability of the orally administered cannabinoids THC and CBD was tested at 6% compared to 27% when inhaled. The bioavailability of pharma kinetics of the same dosage Sativex cannabis extract by GW Pharma (10 mg of THC+10 mg of CBD) administered by intraoral spray to the sublingual and buccal mucosal was statically the same as the same as an identical dose of the orally administered cannabinoid. The lack of a statistical difference between oral THC and oral mucosal spray Sativex 11-OH-THC/THC ratios would indicate that Sativex spray is not being absorbed through the oral mucosa and passing into the systemic circulation. Rather the composition is being swallowed and passing into the GI tract for absorption and the THC is undergoing gastric degradation first pass liver metabolism before reaching the systemic circulation.

Consequentially, cannabinoids require high doses in order to reach therapeutic plasma concentrations after oral and intraoral mucosal administration. Their low bioavailability of 6% may contribute towards the occurrence of their adverse effects.

Dissolution rate is a function of the surface area of the particles and solubility. The surface area can be determined through the control of the particle size. Therefore, the bioavailability of cannabinoids can be improved by reduction in their particle size that increases surface area and encapsulating them in the lipid nanoparticle delivery system of this invention.

The phospholipid lipid nanoparticles encapsulations of cannabinoids in this disclosure both reduce the particle size of cannabinoids and encapsulates them in a dynamic phospholipid membrane carrier to improve passage across the cell membrane barriers of the GI tract, oral mucosa, nasal mucosa and dermal mucosa. The phospholipid lipid nanoparticles encapsulations of cannabinoids in this disclosure improve, increase cannabinoid bioavailability, cannabinoid receptor binding, reduce the required dosages for therapeutic activity and decrease the occurrence of adverse effects from cannabinoid administration.

Toxicity of Polymer Carriers of Cannabinoids

Nanoparticle/polymer carriers of cannabinoids formed from natural and synthetic polymers have been investigated. Studies show solubility and dissolution improvement of the synthetic cannabinoid CB13 (1-Naphthalenyl[4-(pentyloxy)-1-naphthalenyl]methanone) loaded into PLGA polymer nanoparticles were shown. Other studies have used cyclodextrin complexes to improve cannabinoid bioavailability.

Polymer carrier structures include a wide range of surfactants, emulsifiers and excipients in their molecular compositions. Polymer nanoparticles are recognized to contain toxic monomers and solvents that form toxic degradation products. From the past studies of polymeric nanoparticles exhibiting cytotoxic effects, the safety profile of current polymer carriers of cannabinoids is not encouraging or not reported extensively so as to conclude that they are a safe carrier for cannabinoids. By contrast, the cytotoxicity of lipid nanoparticles can be minimal or absent, due to their better physiological acceptability when compared to polymeric nanoparticles.

Safety Considerations of Cannabinoid Nanoparticles

At the nanoscale, the physical and chemical properties of materials differ in fundamental ways from the properties of the atoms and molecules of bulk materials. These effects occur because reduced particle size exponentially increasing the surface area for biological interactions and increased ability of the nanoparticle to cross biological membranes and excipients to alter metabolism. The various combinations of polymers, surfactants, emulsifiers and excipients used the different techniques described in the literature for producing nanostructured carriers of cannabinoids can produce adverse effects, including toxicity and inflammation. There is inadequate testing of many of these ingredients for safety in nanocarriers and these techniques of manufacturing nanoparticles to conclude they are safe for commercial drug applications.

Phospholipid nanoparticles can be manufactured with biocompatible, physiological and GRAS structural materials and excipients that degrade quickly into non-toxic compounds that are easily eliminated through physiologic metabolic pathways and endogenous enzymes. The lipid matrix degradation occurs mostly by lipases whereas only non-enzymatic hydrolytic processes degrade a minor part. Lipid carriers prepared with several lipids and emulsifying agents have shown low toxicity in humans.

Surfactants are important excipients frequently used in nanoparticulate systems as stabilizers and solulibilizers. There are many commercially available surfactants. They have different properties and the same surfactant may have a wide range of applications. The pharmaceutical surfactants lecithin; phosphadylcholine fractions, poloxamer, sodium cholate and polysorbate 80 are well tolerated and non-toxic in nanoparticles. They are unlikely to induce allergic reactions, hypersensitivity or cytokine production.

Cytotoxicity of lipid nanoparticles can occur due to the inclusion of unsafe components such as non-ionic emulsifiers and harmful preservatives. The method of manufacturing a lipid nanoparticle can risk contamination. Methods like solvent evaporation and emulsification; emulsification-solvent diffusion technique and micro emulsion technique can produce nanoparticles with toxic solvent residues left over from product production or high levels of surfactants and other excipients that cause toxicity.

This disclosure teaches production techniques of phospholipid nanoparticle comprising of milling, homogenation and ultrasonic processing that use biocompatible, physiological and GRAS excipients have produced lipid nanoparticle structures showing minimal toxicity.

Intraoral Sublingual Delivery of Nanoparticle Cannabinoids

The absorption of the lipid nanoparticle drugs through the sublingual route is 3 to 10 times greater than the oral route and is only surpassed by hypodermic injection. Sublingual administration of a cannabinoid avoids contact with the GI tract and avoids barrier functions of the GI tract and the first passage of the drug in the liver where some of the cannabinoid is metabolized to inactivity.

Transdermal Delivery of Nanoparticle Cannabinoids

In transdermal administration, the Cannabinoid pass the stratum corneum layer to reach lower layers of the skin and/or to enter systemic circulation. Several formulation approaches for cutaneous administration of cannabinoids have proposed in conventional pharmaceutical forms and vehicle preparations, including topical patches creams, salves and ointments. Studies found transdermal delivery achieved a sustained and steadier action than inhalation or oral administration of the cannabinoid THC.

Intranasal Delivery of Nanoparticle Cannabinoids

Transmucosal routes of drug delivery via mucosal linings of the nasal cavity show distinct advantages over peroral administration for systemic drug delivery. Compared to other biological membranes, the nasal mucosa is a rather porous and thin endothelial basal membrane. It also has a rapid blood flow, with a highly vascularized epithelial layer and a vast absorption area with microvilli in epithelial cells. The passage of drugs across the nasal mucosa occurs in three ways: paracellular, transcellular or transcytotic.

The proven advantages for intranasal delivery of cannabinoids include bypassing first pass effect, avoiding presystemic metabolism, achieving rapid systemic therapeutic blood levels, increasing cannabinoid bioavailability, increasing bioactivity and increasing the therapeutic index. The cannabinoid cannabidiol (CBD) was absorbed intranasally within 10 minutes into the systemic circulation with a bioavailability of 34-46%.

Intranasal delivery can enable the transport of cannabinoids into the central nervous system in a few 25 minutes along the olfactory and trigeminal neuronal pathways. Smaller sized lipid nanoparticle compositions are recognized for direct nose-to-brain drug delivery of lipophilic drugs via intransal administration. The highest concentration of nanoparticles delivered through the nose ends up in the olfactory bulb, medulla, and brainstem at the entry point of the trigeminal nerves. However, widespread delivery to the striatum and cortex also occurs.

General Compositions

This disclosure relates to phospholipid nanoparticle compositions of cannabinoids formed from phospholipids and simpler lipids in an unfired sequential process that encapsulate a high concentration of cannabinoids; increase cannabinoid transport across hydrophobic mucosa; increase the bioavailability of the cannabinoid 2-fold to 8-fold, decrease the dose of cannabinoids 2-fold to 8-fold less than an amount of cannabinoids needed to illicit the same therapeutic effect compared to raw and non-encapsulated cannabinoids; where the nanoparticle structure reduces the adverse effects of cannabinoids; and enable safe, more efficacious cannabinoid therapy.

The disclosure provides methods of delivering phospholipid nanoparticle carrier compositions of cannabinoids as NanoSphere liquid gels for effective cannabinoid therapy; and circumvents the intrinsic problems of inhalation, oral and intraoral delivered cannabinoid compositions.

The disclosure provides phospholipid nanoparticle carrier compositions of cannabinoids where the nanoparticle carriers' constituents include the essential phospholipid phosphatidylcholine and method of delivery that reduce adverse effects of the cannabinoids; and increase cannabinoid bioavailability and therapeutic activity.

The disclosure provides phospholipid nanoparticle carrier compositions of cannabis and methods of delivery where the nanoparticle carrier or constituents act to reduce adverse effects of the cannabinoid and increase cannabinoid bioavailability, therapeutic activity and therapeutic index for long term and safe cannabinoid therapy.

The disclosure provides phospholipid nanoparticle carrier compositions of cannabinoids for delivery into the systemic circulation across the GI tract mucosal barrier, and where the nanoparticle carrier and phospholipid constituents act to reduce effects of the cannabinoids, and increase cannabinoids bioavailability and therapeutic activity.

The disclosure provides phospholipid nanoparticle carrier compositions of cannabinoids for administration and delivery into the systemic circulation across the sublingual or buccal oral mucosal barrier where the nanoparticle carriers increase cannabinoids bioavailability and therapeutic activity.

The disclosure provides phospholipid nanoparticle carrier compositions of cannabinoids for administration and delivery into the systemic circulation across the epidermal and dermal barriers and to where the nanoparticle carriers increase cannabinoids bioavailability and therapeutic activity.

The disclosure provides phospholipid nanoparticle carrier compositions of cannabinoids' administration and delivery into the systemic circulation across the mucosal barrier of the nasal cavity where the nanoparticle carriers increase cannabinoids bioavailability and therapeutic activity.

The disclosure provides phospholipid nanoparticle carrier compositions of cannabis and methods of delivery where the nanoparticle carrier composition or constituents that deliver standardized and precision-metered dosages of cannabinoids suited for oral, intraoral, intranasal and/or transdermal administration.

General Methods for Making the General Compositions

The disclosure teaches a process for producing phospholipid lipid structural nanoparticle carrier compositions of cannabinoids that are formed from essential phospholipids (phosphatidylcholine) and lipids.

The disclosure teaches a process for producing phospholipid lipid structural nanoparticle carrier compositions of cannabinoids and phytochemicals of the cannabis plant that are formed from phospholipids and lipids.

The disclosure teaches a process for producing phospholipid lipid structural nanoparticle carrier compositions of cannabis extract that are formed from phospholipids and lipids.

The disclosure teaches a process for producing phospholipid lipid structural nanoparticle carrier compositions of CBD hempseed oil extract that are formed from phospholipids and lipids.

The disclosure teaches a process for producing phospholipid lipid nanoparticle carrier compositions of cannabinoids and phytochemicals of the cannabis plant where the production method is free of polymers.

The disclosure teaches a process for producing phospholipid lipid nanoparticle carrier compositions of cannabinoids where the production method is free of non-biocompatible and non-biodegradable surfactants.

The disclosure teaches a process for producing phospholipid lipid nanoparticle carrier compositions of cannabinoids where the production method is free of non-biocompatible, non-biodegradable surfactants, solvents and/or expedients that cause adverse and cytoxic effects as nanoparticles.

The disclosure teaches a process for producing phospholipid lipid structural nanoparticle carrier composition that provides a composition efficiently encapsulating a high concentration and a high percentage of a cannabinoid or a mixture of cannabinoids and phytochemicals of the cannabis plant comprising a production method incorporating nanoparticle production schemes. This phospholipid lipid nanoparticle carrier system is used for the delivery of cannabinoids into mammals.

The disclosure teaches a process for producing phospholipid lipid nanoparticle carrier compositions of cannabinoids where the production method comprises a combination of milling, homogenization, and ultrasonic processing in sequence in sequence that localizes cannabinoids in and on the outer membrane of the nanoparticle and targets receptors of the endocannabinoid system.

In one embodiment, the disclosure teaches a method of assembly for producing phospholipid lipid nanoparticle carrier compositions of cannabinoids where the production method comprises two of the three techniques of milling homogenization, and ultrasonic processing in a unified sequence.

In one embodiment, the disclosure teaches a method of assembly for producing phospholipid lipid nanoparticle carrier compositions of cannabinoids where the production method comprises homogenization and ultrasonic processing in a unified sequence.

In one embodiment, the disclosure teaches a method of assembly for producing phospholipid lipid nanoparticle carrier compositions of cannabinoids where the production method comprises homogenization. In one embodiment, the disclosure teaches a method of assembly for producing lipid nanoparticle carrier compositions of cannabinoids in standardized and precision-metered dosages.

The disclosure teaches a method of forming phospholipid lipid nanoparticle carrier compositions of cannabinoids comprising the full range of phytocannabinoids and phytochemicals found in cannabis concentrates and cannabis extracts.

The disclosure teaches a method of forming phospholipid lipid nanoparticles carrier compositions of cannabinoids comprising a mixture of phytocannabinoids and phytochemicals concentrated and extracted from cannabis sativa.

The disclosure teaches a method of forming phospholipid lipid nanoparticles carrier compositions of cannabinoids comprising phytocannabinoids that are concentrated and extracted from hempseeds.

The disclosure teaches a process for producing phospholipid lipid nanoparticle carrier compositions of cannabinoids that localizes cannabinoids in and on the outer membrane of the nanoparticle.

The disclosure teaches a process for producing phospholipid lipid nanoparticle carrier compositions of cannabinoids that localizes cannabinoids in and on the outer membrane of the nanoparticle and targets receptors of the endocannabinoid system.

The disclosure teaches a process for producing phospholipid lipid nanoparticle carrier compositions of cannabinoids where the production method comprises a combination of milling, homogenization and ultrasonic processing in sequence that does use hot techniques and nanoparticle production methods causing degradation to cannabinoids and phytochemicals of the cannabis plant.

The disclosure teaches a nanoparticle method of assembly wherein the assembly comprises three assembly techniques in a sequential unified process without hot techniques, without polymers that encapsulate cannabinoids with biocompatible biodegradable essential phospholipids, lipids and solvents that are FDA approved and safe as nanoparticles.

The disclosure teaches a nanoparticle method of assembly wherein the assembly comprises three assembly techniques in a sequential unified process without the use of hot techniques, without polymers that encapsulate cannabinoids, with biocompatible non-toxic biocompatible essential phospholipids, lipids, surfactants, solvents and excipients that are FDA approved and safe as nanoparticles.

The disclosure teaches a process for producing phospholipid lipid nanoparticle carrier compositions of cannabinoids where the production method is free of surfactants, solvents and/or expedients that cause toxicity, inflammation and adverse effects as nanoparticles.

The disclosure teaches a process for producing phospholipid lipid nanoparticle carrier compositions of cannabinoids that localizes cannabinoids in and on the outer membrane of the nanoparticle.

The disclosure teaches a process for producing phospholipid lipid nanoparticle carrier compositions of cannabinoids that localizes cannabinoids in and on the outer membrane of the nanoparticle and targets receptors of the endocannabinoid system.

The disclosure teaches a process for producing phospholipid lipid nanoparticle carrier compositions of cannabinoids where the production method comprises a combination of milling, homogenization and ultrasonic processing in sequence using cold techniques in each step. At least one cannabinoid is incorporated into the process, effective for administration to mammals.

The disclosure teaches a nanoparticle method of assembly wherein the assembly comprises three assembly techniques in a sequential unified process without the use of heat, without polymers that encapsulate cannabinoids with biocompatible biodegradable essential phospholipids, simpler lipids and solvents that are FDA approved and safe as nanoparticles.

The disclosure teaches a process for producing phospholipid lipid nanoparticle carrier compositions of cannabinoids and phytochemicals of the cannabis plant where the production method is free of surfactants, solvents and/or expedients that cause cytotoxicity, inflammation and adverse effects as nanoparticles.

The disclosure teaches a process for producing phospholipid lipid structural nanoparticle carrier composition that provides a composition including a high concentration of cannabinoids and phytochemicals of the cannabis plant comprising a production method incorporating nanoparticle production schemes. This phospholipid lipid nanoparticle carrier system is used for the delivery of cannabinoids into mammals.

The disclosure teaches a process for producing phospholipid lipid nanoparticle carrier compositions of cannabinoids where the production method comprises a combination of milling, homogenization and ultrasonic processing in sequence using cold techniques in each step, and is effective for administration to mammals.

The disclosure teaches a nanoparticle method of assembly wherein the assembly comprises three assembly techniques in a sequential unified process without hot techniques, without polymers that encapsulate cannabinoids with biocompatible non-toxic biocompatible essential phospholipids, simpler lipids and solvents that are FDA approved and safe as nanoparticles.

The disclosure teaches a nanoparticle method of assembly wherein the assembly comprises three assembly techniques in a sequential unified process without the use of hot techniques, without polymers that encapsulate cannabinoids with biocompatible non-toxic biocompatible essential phospholipids, simple lipids, surfactants, solvents and excipients that are FDA approved and safe as nanoparticles.

The disclosure teaches a process for producing phospholipid lipid nanoparticle carrier compositions of cannabinoids where the production method comprises a combination of milling, homogenization and ultrasonic processing in sequence.

The disclosure teaches a process for producing phospholipid lipid nanoparticle carrier compositions of cannabinoids where the production method comprises a combination of milling, homogenization and ultrasonic processing in sequence that localizes cannabinoids in and on the outer membrane of the nanoparticle and targets receptors of the endocannabinoid system.

In one embodiment, the disclosure teaches a method of assembly for nanosphere compositional structures wherein the method of assembly efficiently encapsulates cannabinoids into a stable phospholipid nanoparticle structure with a particle size distribution from 50 to 150 nm. This method of assembly allows for commercial production.

In one embodiment, the disclosure teaches a method of assembly for nanosphere compositional structures wherein the method of assembly efficiently encapsulates cannabinoids into a phospholipid nanoparticle structure that contains ligands and/or coatings and/or specific surface charges to improve cannabinoid transport across cell membranes, improve cannabinoid-to-receptor binding and decrease adverse effects.

The disclosure teaches a nanoparticle method of assembly wherein the assembly comprises three nanoparticle assembly techniques in a sequential unified process encapsulating cannabinoids. The nanoparticles are stable phospholipid nanoparticle compositional structures with a particle size distribution from about 50 to 150 nm. The assembly can be scaled for commercial production and scalable to commercially available size production.

The disclosure teaches a nanoparticle method of assembly wherein the assembly comprises three nanoparticle assembly techniques in a sequential unified process encapsulating cannabinoids. The nanoparticles are stable phospholipid nanoparticle compositional structures that provide standardized precision-metered dosages of cannabinoids for methods of delivery that include oral, intraoral, intranasal and transdermal administration.

The disclosure teaches a nanoparticle method of assembly wherein the assembly comprises three nanoparticle assembly techniques in a sequential unified process encapsulating cannabinoids. The nanoparticles are stable phospholipid nanoparticle compositional structures that provide standardized precision-metered dosages of cannabinoids as viscoelastic gels for methods of delivery that include oral, intraoral, intranasal and transdermal administration.

The disclosure further teaches the products for administration via the sublingual mucosa and buccal mucosa of a mammal. The disclosure further teaches a product, by the process disclosed above, for transdermal administration across dermal and epidermal barriers. The disclosure further teaches a product, by the process disclosed above, for administration across the gastrointestinal (GI) tract mucosal barrier. The disclosure further teaches a product, by the process disclosed above for administration across the nasal mucosal barrier.

The disclosure further teaches a method for producing a cannabinoid for delivery via the sublingual mucosa and buccal mucosa of a mammal for cannabinoid therapy and the reduction of cannabinoid adverse effects.

The disclosure further teaches a method for producing a cannabinoid for administration across dermal and epidermal barriers for cannabinoid therapy and the reduction of cannabinoid adverse effects.

The disclosure further teaches a method for producing a cannabinoid for administration across the GI tract mucosal barrier for cannabinoid therapy and the reduction of cannabinoid adverse effects.

The disclosure further teaches a method for producing a cannabinoid for administration across the nasal mucosal barrier for cannabinoid therapy and the reduction of cannabinoid adverse effects.

The disclosure further teaches a method for encapsulating a cannabinoid into a phospholipid nanoparticle for delivery into the systemic circulation via the sublingual mucosa and buccal mucosa of a mammal for cannabinoid therapy.

The disclosure further teaches a method for encapsulating a cannabinoid into a phospholipid nanoparticle composition, for delivery into the systemic circulation across the GI tract mucosal barrier for cannabinoid therapy.

The disclosure further teaches a method for encapsulating a cannabinoid into a phospholipid nanoparticle composition for delivery across dermal and epidermal barriers into the systemic circulation for cannabinoid therapy.

The disclosure further teaches a method for encapsulating a into a phospholipid nanoparticle for delivery across the mucosa barrier of the nasal cavity into the systemic circulation for cannabinoid therapy.

The disclosure teaches formulating phospholipid lipid nanoparticles containing cannabinoids into solid dose forms including dissolvable tablets, granule, gums, lozenges, pellets, and other forms for intraoral delivery by sublingual and buccal administration. Suitable formulation methods include spray drying of lyophilization of lipid structured nanoparticle dispersions with suitable excipients followed by incorporation of a dry powder into a tablet, or pellet. Another method is granulating phospholipid nanoparticles liquid dispersions with excipients and binders into powders for compression into tablets or pellets for sublingual and buccal delivery. Phospholipid nanoparticles may be incorporated into lozenges, lollipops, gum, gels and films for intra-oral delivery.

The disclosure teaches a method of forming phospholipid lipid nanoparticles comprising of at least one of the phytocannabinoids found in cannabis that include delta-9-tetrahydrocannabinol (THC), cannabidiol (CBD), cannabinol (CBN) cannabigerol (CBG), cannabigerol (CBG), cannabichromene (CBC), cannabicyclol (CBL), canabivarol (CBV), tetrahydrocannabivarin (THCV), cannabidivarin (CBDV), cannabichromevarin (CBCV), cannabigerol monoethyl ether (CBGM).

The disclosure teaches a method of forming phospholipid lipid nanoparticles comprising the full range of phytocannabinoids and phytochemicals found in cannabis extract.

The disclosure teaches a method of forming phospholipid lipid nanoparticles comprising of at least one of the botanical cannabimimetics include N-alkylamides from Echinacea and B-caryophyllene.

The disclosure teaches a method of forming phospholipid lipid nanoparticles comprising synthetic cannabinoids.

The disclosure teaches a method of forming phospholipid lipid nanoparticles comprising pure cannabinoids.

The disclosure teaches a method of forming phospholipid lipid nanoparticles comprising a mixture of phytocannabinoids and phytochemicals extracted from cannabis sativa.

The disclosure teaches a method of forming phospholipid lipid nanoparticles comprising phytocannabinoids extracted from hempseeds.

The disclosure teaches a method of making nanoparticle compositions of cannabinoids formed from phospholipids and simpler lipids and in an unfired sequential process. The disclosure teaches standardized precision-metered dosage forms of cannabinoids for different routes of delivery. The disclosure teaches increasing cannabinoid transport across hydrophobic mucosa; increasing the bioavailability of the cannabinoid delivered; decreasing the dose of cannabinoids needed to illicit the same therapeutic effect compared to raw and non-encapsulated cannabinoids.

Phospholipid Nanoparticle Compositions of Cannabinoids

Many synthetic polymers and even natural polymers can have toxic properties and produce adverse biological in humans. Most polymers have not been tested as nanoparticles at this time to recommend them safe for human use. For example, both synthetic and natural polymers may act upon the complement system. Natural polymers can lead to lead to cellular and humoral immune responses from being recognized as foreign substances.

For example, polyethylene glycol (PEG) and its derivatives are widely used polymers and non-ionic surfactants. PEG is a hydrophilic biocompatible and non-biodegradable nanoparticle biomaterial. PEG is degraded by oxidative degradation under biologically relevant conditions. The generation of reactive oxygen species (ROS) may have biological consequences. PEG has the propensity to induce blood clotting and clumping of cells. Diverse reactions of PEG often occur through complement (C) activation, which leads to hyper-sensitivity reactions (HSR).

As a result, the types of nanoparticles used as nanoparticle carriers of cannabinoids in this disclosure are phospholipid/lipid nanoparticles. Lipid nanoparticles are known for their high degree of biocompatibility, controlled release, efficient targeting, stability, natural biodegradability and high therapeutic index to their payload.

Lipid nanoparticles may be assembled as solid lipid nanoparticles (SLN), nanostructured lipid carriers (NLC), and NanoSpheres (NS). The preferred cannabinoid lipid nanoparticle carrier assemblies of this disclosure are NanoSpheres (NS).

Nanoemulsions (NE) are carrier systems in the nanometer size comprising a continuous aqueous phase and at least one dispersed oily phase, in which the oily phase comprises at least one amphiphilic lipid such as phospholipids and at least one solubilizing lipid with a monolayer around an amorphous core.

"Solid lipid nanoparticles (SLN)" are colloidal drug carriers and dynamic structures that are typically synthesized from phospholipids, lipids, and excipients. They are composed of an outer phase membrane of lipids and/or phospholipids and an inner phase solid lipid inner core. SLN have a mean particle size in the nanometer range. SLN combine the advantages of emulsions, liposomes and polymeric nanoparticles. The solid matrix can protect incorporated active ingredients against chemical degradation and provide the highest flexibilities in the modulation of the drug release profiles. SLN provide controlled release, efficient targeting, and stability. SLN are particulates structurally related to polymeric nanoparticles. However, in contrast to polymeric systems, SLN can be composed of biocompatible lipids that are physiologically well tolerated when administered in vivo and may also be prepared without organic solvents.

"Nanostructured lipid carriers (NLC)" are colloidal carriers and a second generation evolvement of SLN. NLC are characterized by an outer phase phospholipid and/or lipid membrane and an inner phase lipid core consisting of a mixture of solid and liquid lipids. NLC have a mean particle size in the nanometer range. NLC a controlled nanostructuring of the lipid matrix is performed due to the mixture of solid and liquid lipids, in order to increase drug-loading and prevent its expulsion. In addition, the NLC nanostructured lipid matrix gives more flexibility in modulation of drug release. NLC are composed of a lipid matrix of cannabinoids with a nanostructure that improves cannabinoid loading and firmly retains the cannabinoids during storage.

"NanoSpheres (NS)" are dynamically structured highly stable lipid nanoparticles in the form of nanosized viscoelastic gels. Their viscosities are controlled in comparison to SLN and NLC. NanoSpheres are synthesized from biocompatible, and biodegradable essential phospholipids, lipids, and excipients in a unified sequential process. NanoSpheres in this disclosure are characterized by an outer phospholipid membrane and adjustable viscoelastic lipid gel core containing cannabinoids. NanoSpheres have a mean particle size in the nanometer range.

The lipid dispersed phase weight fraction, dispersed cannabinoid load phase weight fraction, solvent and carrier system fraction characteristics, and the phospholipid membrane's characteristics determines the NanoSpheres viscosity and viscoelastic properties. The fluidity and viscoelastic properties of the NanoSpheres phospholipid membrane and core's properties favorably influences properties such as cannabinoid transport across cell membranes, binding to receptor sites and signal transduction.

The adjustable viscoelastic lipid gel core of NanoSphere phospholipid nanoparticles improves cannabinoid loading, and enables administering cannabinoids in precision-metered dosages through different routes of administration that encompass intranasal, intraoral, peroral and transdermal routes of administration.

NanoSpheres firmly retain the cannabinoids during storage, are stable structures and provide high-loading efficiencies. Nanospheres present numerous advantages over other carrier formulas. They are biocompatible, biodegradable and can easily be produced by the versatile and up-scalable unified sequential assembly process of this disclosure.

The internal physical state of lipid core nanoparticles has been shown to dramatically affect their encapsulation and release properties. SLN have limited controllability. Crystallization of their lipid core generally leads to separation of encapsulated agents from their lipid core and expulsion causing a high burst release.

NLC are composed of a mixture of liquid and solid lipids that produce less crystallization in their core. This enables a better encapsulation ratio and control over release kinetics.

NanoSpheres that are formed from phospholipids, lipids and excipients in a unified sequential process of milling, homogenization and ultrasonic processing are very stable. They're comprised of an amorphous viscoelastic internal core and external membrane for characteristics of long-term stability and a desirable high-encapsulation, localization and release behavior of their cannabinoid payloads.

The Localization of cannabinoids in lipid nanoparticles affects their release and bioactivity. In lipid nanoparticles they can either be can be distributed homogenously throughout the entire nanoparticle's matrix or more likely be distributed in relatively different amounts in different regions of the nanoparticles. Cannabinoids and other phytochemicals in cannabis extract can be localized in their inner core, attached to the surface of the outer membrane, and be localized in the outer membrane of lipid nanoparticles.

Nanosphere phospholipid nanoparticles are optimized for localizing lipophilic cannabinoids inside and on the outer surface of the phospholipid lipid membrane. Between 20-35% of the encapsulated material can be localized in and on the lipid membrane based on test models.

Attaching the cannabinoids THC, CBD and others in cannabis extract to the membrane surface in the membrane of Nanospheres enables the efficient targeting of endocannabinoid system receptor located in brain and throughout the body for therapeutic activity.

The physical properties of the phospholipid nanoparticle vesicles of this disclosure are similar to those of native cell membranes in which the cellular interior is isolated from the external environment by lipid and protein-rich dynamic boundaries.

The highly purified essential phospholipid phosphatidylcholine fractions forming the structural material of the phospholipid nanoparticles in this disclosure are known as a "membrane therapeutic". They improve the integrity of the cell membrane and up-regulates the fluidity of the cell membrane.

Their membrane dynamics in the smaller size (less than 100 nm diameter and preferably) and spherical shaped lipid nanoparticle carriers of this disclosure can improve the pathway of cannabinoid to cannabinoid receptor coupling in the lipid bilayer of the cell membrane for greater therapeutic bioactivity, prevent adverse effects from the administration of cannabinoids and decrease developing a tolerance to cannabinoids during therapy.

The phospholipids in the process of synthesizing the phospholipid nanoparticle compositions encapsulating cannabinoids in this disclosure include phosphatidycholine, phosphatidylethanolamine, phosphatidylglycerol, phosphatidylserine, phosphatidylinositol, cardiolipin, and the derivatives of these phospholipids. Preferred phospholipids in lipid nanoparticles of this disclosure should be biocompatible, GRAS listed and non-toxic as nanoparticles.

Suitable commercially available natural essential phospholipids from soya lecithin fractionation for this disclosure include Lipoid Phospholipon 80, 80 N, 80 H 85 G, 90 G, 90 H and 100 H; and Lipoid's solubilized lecithin liquid carrier systems that include Phosal 35 B. 50 SA, 53 MCT and 75 SA.

The lipids in the process of synthesizing the lipid structured nanoparticle compositions in this disclosure may include fatty acids, triglycerides triacylglycerols, acylglycerols, fats, waxes, cholesterol, sphingolipids, glycerides, sterides, cerides, glycolipids, sulfolipids, lipoproteins, chylomicrons and the derivatives of these lipids. The preferred simpler lipids in this disclosure are medium chained triglycerides, hemp seed oil, safflower oil and sesame oil. Preferred simpler lipids used in forming phospholipid nanoparticles of this disclosure should biocompatible, GRAS listed and non-toxic as nanoparticles.

The preferred of weight/volume ratios of phospholipids to simpler lipids in forming phospholipid nanoparticles of this disclosure is from 4:1 to 1:4. Preferably, the weight ratio is from about 2:1 to about 1:2.

The preferred percentage of weight/volume ratios of cannabinoids to phospholipid nanoparticle structural materials (phospholipids+lipids) in forming phospholipid nanoparticles of this disclosure is from 4:1 to 1:5. Preferably, the weight ratio is from about 3:1 to about 1:2.

Surfactants are surface tension lowering compounds used as emulsifiers, solubilizers, and dispersants in the assembly of nanoparticles. They're a surface active group of amphiphilic molecules which are manufactured by chemical processes or purified from natural sources or processes. These can be anionic, cationic, nonionic, and zwitterionic.

Surfactants may be selected to provide coatings and functional groups on the nanoparticle membrane, alter the membrane surface charge adjust the core's viscoelastic properties, and alter nanoparticle's physiological behavior.

The assembly of the phospholipid nanoparticle compositions of cannabinoids in this disclosure may include biocompatible and biodegradable surfactants such lecithins, polysorbates, monoglycerides, diglycerides, triglycerides, glyceryl oleate, polaxamers and other non-toxic, non-ionic surfactants that are known to the art.

Surfactants that should not be used in assembly of the nanoparticle compositions of this disclosure are surfactants that are not biocompatible, not biodegradable and produce adverse biological interactions. Surfactants that should not be used in assembly of nanoparticle compositions of this disclosure include ionic, synthetic, and polymer surfactants recognized as toxic and irritants.

For example, Polyethylene glycol (PEG) is a non-biodegradable non-ionic surfactant PEG that can induce blood clotting and clumping of cells, generate ROS species and induce adverse immunological reactions which leads to hyper-sensitivity reactions (HSR).

The preferred surfactant for making lipid nanoparticles in this disclosure is lecithin, the source of the essential phospholipids forming the outer membrane of lipid nanoparticles. The phospholipids present in liquid lecithin phosphatidylcholine phosphatidylethanolamine, phosphatidylinositol and phosphatidic acid.

Lecithins work as emulsifiers dispersing normally unmixable material into another by mixing, colloidal milling or homogenization. Their surface-active simultaneous hydrophilic and hydrophobic properties enable lecithin to make stable blends of biomaterials that otherwise do not mix. Lecithins can provide fast, complete wetting of powders into aqueous systems.

An important function of lecithin in the assembly of phospholipid nanoparticle of this disclosure is modifying the viscosity of liquids and semi-liquids of the inner core in forming adjustable viscoelastic gels for precision dose-metered dosages of cannabinoids.

Suitable and synergistic surfactants to lecithin in the assembly of phospholipid nanoparticles of this disclosure are polysorbates (Tweens). They are non-ionic liquids used as surfactants for dispersing hydrophobic particles in aqueous solutions ion the assembly of lipid nanoparticles of this disclosure. Polysorbate 80 is a polyethylene sorbitol ester, also known as Tween 80, sorbitan monooleate, polyoxyethylenesorbitan monooleate is used for emulsifying and dispersing substances. Polysorbate 20 is a polyoxyethylene sorbitol ester member of the polysorbate family used as emulsifying agents for the preparation of stable oil-in-water emulsions.

The assembly of the phospholipid nanoparticle compositions of cannabinoids in this disclosure may include ligands formed from biocompatible materials and functionalized to bind to the nanoparticles for the construction of geometric nanostructures.

The assembly of the phospholipid nanoparticle compositions of cannabinoids in this disclosure may include surfactants that are biocompatible and biodegradable. They include lecithins such as Alcolec S, Alcolec BS and Alcolec XTRA-A, polysorbates such as Polysorbate 80 and Polysorbate 20, monoglycerides, diglycerides, triglycerides, glyceryl monoleate, polysorbates polaxamers and other nontoxic ionic and ionic surfactants that are known to the art. Surfactants may be selected to provide coatings and functional groups on the nanoparticle membrane and alter the membrane surface charge for greater transport of cannabinoids across cell membranes, binding to receptor sites and signal transduction.

In one embodiment of this disclosure, non-bilayer lipids are used in place of or in conjunction with phospholipids in an assembly method for producing lipid nanoparticle carrier compositions of cannabinoids. These lipids include fatty acids such stearic acid, palmitic acid, belenic acid, myrisitic acid and oleic acid; free fatty acid alcohols such as stearyl alcohol, cetyl alcohol, myristyl alcohol, lauryl alcohol; triglycerides such as trimyristin, tripalmitin, trilaurin; waxes such as bees wax, cetyl palmitate, carnuba wax, cannabis wax extract; mono, di and triglycerides mixtures such as Suppocire NC, witepsol bases, glyceryl monostearate, glyceryl behenate, palmitostearate, and softisan; and others such as cacao butter, castor oil, anhydrous milk fat, and hydrogenated palm oil.

In one embodiment of this disclosure, Suppocire NC is used in conjunction with lipids in an assembly method for producing phospholipid lipid nanoparticle carrier compositions of cannabinoids and nanoparticle viscoelastic gels.

Surfactants should be selected that do not induce adverse changes in barrier functions, do not induce toxic and allergic effects, do not induce adverse effects to the nanoparticles, and do not induce adverse effects to the transported cannabinoids. Preferred surfactants in nanoparticles of this disclosure should be biocompatible, biodegradable GRAS listed and non-toxic as nanoparticles.

Surfactants excluded from assembly of the phospholipid nanoparticle compositions of cannabinoids in this disclosure include ionic and synthetic surfactants recognized to be toxic and irritants.

The assembly of the phospholipid nanoparticle compositions of cannabinoids in this disclosure includes a solvent and carrier fluid system. Suitable carrier fluids and solvents include water, sterile saline, glycerides glycerine, and ethanol, sorbitol, lipids, fatty acids, glycine, and silicone oils; and their dispersions emulsions, suspensions, mixtures, self-assembly and other methods of incorporation in the assembly of nanoparticles. Suitable carrier fluids and solvents should be GRAS listed, biocompatible, biodegradable and non-toxic as nanoparticles.

The assembly of the phospholipid nanoparticle compositions in this disclosure may include preservatives selected according to the route of delivery, barrier function, properties of nanoparticle materials, and properties of the encapsulated cannabinoids. Plus, preservatives should be selected that do not induce changes in barrier functions, do not induce toxic and allergic effects, do not induce adverse effects to the nanoparticles, and do not induce adverse effects to the transported cannabinoids. Some of the preservatives for consideration in use include tocopherols, ascorbyl palmitate, sorbates, parabens, optiphen, thimersal, benzoic acid, benzalkonium chloride, benzehtkonium chloride polyquaternium-1, ethyl lauroyl arginate, and rosemary oleoresin, Jeecide and Optiphen.

The preservatives in this disclosure include but are not limited to tocopherols, ascorbyl palmitate and sorbates for intraoral and peroral administered formulations; benzalkonium chloride, benzehtkonium chloride for ocular and intranasal administered formulations; and sorbates, Jeecide and Optiphen for transdermal administered formulations. Preferred preservatives in phospholipid nanoparticles of this disclosure should be biocompatible, GRAS listed and non-toxic as nanoparticles. Preferred preservatives should not interfere with the delivery of the cannabinoids.

Nanoparticle size, shape, functional groups on their surface coatings and their membrane charge are extremely important to the biological properties and effectiveness of cellular uptake of the nanoparticle cannabinoid carriers of this disclosure. Nanoparticles with 50 nm show the most efficiency of uptake. Furthermore spherical particles of similar size were taken up 500% more than rod-shaped particles.

The small nanoparticle sizes and the spherical shape of the phospholipid nanoparticle dynamic composition of this disclosure facilitate better endocytotic cell membrane internalization and superior cannabinoid to receptor binding. These results in greater cannabinoid bioactivity in therapy and fewer adverse effects compared to administration of raw and non-encapsulated cannabinoids.

The assembly of phospholipid nanoparticle compositions in the present disclosure may include sweeteners for intraoral and peroral routes of delivery to enhance acceptability to the consumer. The sweeteners used may be natural sweeteners or artificial sweeteners. Natural sweeteners include Stevia extract Steviol Glycosides, xylitol, sucrose, fructose, fructooligosaccharides, glucose, glucose syrup, invert sugar, maltodextrins, Magnasweet, eryritol, sorbitol, maltitol, lactitol, mannitol, and isomalt. Examples of artificial sweeteners include sucralose, aspartame, acesulfame K, neohesperidine, dihydrochalcone, thaumatin, saccharin and saccharin salts. Preferred sweeteners for this disclosure should be sucralose, Acesulfame K and natural sweeteners such as steviol glycosides, xylitol, erythritol and thaumatin. Magnasweet.

Typically the sweetener content will be about 0.05 to 2.5% w/w. Preferred sweeteners in nanoparticles of this disclosure should be biocompatible, GRAS listed and non-toxic as nanoparticles.

The assembly of phospholipid nanoparticle compositions in the present disclosure may include flavors for intraoral and peroral routes of delivery to enhance acceptability to the consumer. The flavors used may be natural sweeteners or artificial sweeteners. Examples of flavoring agents useful in the compositions of the invention include fruit (e.g. pineapple or citrus) concentrates and concentrated aqueous or non-aqueous flavors such as flavor oils. Typically the sweetener content will be about 0.1 to 1% w/w. preferred flavors in phospholipid nanoparticles of this disclosure should be biocompatible, GRAS listed and non-toxic as nanoparticles.

A smaller nanoparticle size and a natural lipid and phospholipid nanoparticle composition (that mimics a plasma lipoprotein), can avoid extensive presystemic metabolism, avoid uptake by the reticuloendothelial system of the liver and spleen as a foreign substance, and prevent premature clearance from the body, is the preferred nanoparticle composition in this disclosure.

This disclosure relates to the significant increase of phospholipid nanoparticles compositions to carry cannabinoids across mucosal barriers into the systemic circulation and across cell membranes to bind with cannabinoid receptors; and increase the bioavailability, bioactivity and efficacy of cannabinoids for therapeutic activity in cannabinoid therapy.

This disclosure relates to the significant increase of phospholipid nanoparticles compositions to carry cannabinoids across mucosa barriers into the systemic circulation and across cell membranes to bind with cannabinoid receptors and decrease the adverse effects of cannabinoids.

The increased bioavailability and bioactivity of cannabinoids can range from a 2-fold increase to 8-fold increase. The actual increase amount depends on the molecular characteristics of the cannabinoid, the encapsulation characteristics into phospholipid nanoparticles, the structural characteristic of the phospholipid nanoparticles, the method and vehicles of administration and metabolic difference between users.

The increase in bioactivity and bioactivity of cannabinoids produced by a phospholipid nanoparticle cannabinoid composition of this disclosure results in dose reduction to produce equivalent therapeutic actions compared to the standard doses of commercial cannabinoid tablets and capsules to illicit a given therapeutic effect response. The dose reduction can range from a 2-fold reduction in mg dose to an 8-fold reduction in mg dose. Preferably, the range is from about a 2-fold reduction to about an 8-fold reduction in mg cannabinoid dose.

The decrease in cannabinoid dosages from a phospholipid nanoparticle cannabinoid composition of this disclosure decreases the occurrence of cannabinoid adverse effects, increases the therapeutic index and has other tangible benefits that include increased patient compliance, increased cost effectiveness.

The process of synthesizing lipid nanoparticles in the present disclosure may include homogenization techniques such as hot high pressure homogenization technique, cold high pressure homogenization technique, melt emulsification ultrasound (ultrasonication) homogenization technique, high shear homogenization and/or ultrasound technique, microemulsion technique, emulsification-solvent evaporation technique, solvent displacement or injection technique, emulsification-solvent diffusion technique, phase inversion technique, film ultrasonication dispersion technique, and multiple emulsion technique.

The disclosure teaches a method for manufacture of lipid nanoparticles by a combination of three techniques, sequentially performed for dispersion comprising milling (physical grinding), homogenization (high speed stirring emulsification) and ultrasonic processing (high wattage flow through ultrasound sonification). These techniques can be performed in this sequential order or may be performed sequentially in alternate orders.

The disclosure teaches a method for manufacture of lipid nanoparticles by homogenization techniques and/or ultrasonic processing.

Administration of Cannabinoid in Phospholipid Nanoparticles by Different Methods This disclosure teaches administration of cannabinoids encapsulated in phospholipid NanoSpheres via the intraoral, intranasal or transdermal methods prevent first pass liver metabolism and maintains relatively consistent plasma levels for long-term cannabinoid therapy.

The Phospholipid Nanoparticle carrier compositions of cannabinoids in this disclosure can be designed for all possible routes of administration, generally improving both bioavailability and bioactivity of the carried cannabinoid or cannabinoids. They represent an alternative class of vehicles to liposomes, emulsions, aqueous solutions, vaporizing, smoking, transdermal patches, chewing gums, edible food forms and solid formed tablets and capsules to for cannabinoid therapy.

Intraoral Transport of Phospholipid Nanoparticle Cannabinoids Compositions Across the Oral Mucosa The disclosure teaches methods of administering phospholipid nanoparticle carrier compositions of cannabinoids to the sublingual mucosa and buccal mucosa of the oral cavity to increase the delivery, absorption and the bioavailability of cannabinoids into the blood stream and to target receptors of mammals.

The disclosure teaches intraoral sublingual or buccal delivery of phospholipid nanoparticle carrier compositions of cannabinoids to increase the cannabinoids, onset of bioactivity, bioavailability, bioactivity, therapeutic activity and therapeutic index in cannabinoid therapy.

The disclosure teaches intraoral sublingual or buccal delivery of phospholipid nanoparticle carrier compositions of cannabinoids to decrease the adverse effects of cannabinoid therapy.

The disclosure teaches intraoral sublingual or buccal delivery of phospholipid nanoparticle carrier compositions of cannabinoids to bypass GI track barriers and eliminate first pass liver metabolism effects with the inclusion of essential phospholipids in the nanoparticle's structural composition.

The disclosure teaches intraoral sublingual or buccal delivery of phospholipid nanoparticle carrier compositions of cannabinoids to deliver standardized and precision-metered dosages.

Peroral Transport of Phospholipid Nanoparticle Cannabinoids Compositions Across the GI Mucosa The disclosure teaches methods of the oral administration of phospholipid nanoparticle carrier compositions of cannabinoids across the mucosal membrane barriers of the GI tract to increase the delivery, absorption and the bioavailability of cannabinoids into the blood stream and to target receptors of mammals.

The disclosure teaches oral administration of phospholipid nanoparticle carrier composition of cannabinoids across the mucosal membrane barriers of the GI tract to increase the cannabinoids bioavailability, bioactivity, therapeutic activity and therapeutic index in cannabinoid therapy.

The disclosure teaches oral administration of phospholipid nanoparticle carrier composition of cannabinoids across the mucosal membrane barriers of the GI tract to decrease the adverse effects of cannabinoid therapy.

The disclosure teaches the oral administration of phospholipid nanoparticle carrier composition of cannabinoids across the mucosal membrane barriers of the GI tract to decrease or eliminate first pass liver metabolism effects with the inclusion of essential phospholipids in the nanoparticle's structural composition.

The disclosure teaches the oral administration of phospholipid nanoparticle carrier composition of cannabinoids across the mucosal membrane barriers of the GI tract to deliver standardized and precision-metered dosages.

Transdermal Transport of Phospholipid Nanoparticle Cannabinoids Compositions Across the Dermis The disclosure teaches methods of transdermal administration of phospholipid nanoparticle carrier compositions of cannabinoids across the epidermis and dermis to increase the delivery, absorption and the bioavailability of cannabinoids into the blood stream and to target receptors of mammals.

The disclosure teaches transdermal administration of phospholipid nanoparticle carrier composition of cannabinoids across the epidermis and dermis to increase the cannabinoids bioavailability, bioactivity, therapeutic activity and therapeutic index in cannabinoid therapy.

The disclosure teaches transdermal administration of phospholipid nanoparticle carrier composition of cannabinoids across the epidermis and dermis to decrease the adverse effects of cannabinoid therapy.

The disclosure teaches the transdermal administration of phospholipid nanoparticle carrier composition of cannabinoids to bypass GI track barriers and eliminate first pass liver metabolism effects with the inclusion of essential phospholipids in the nanoparticle's structural composition.

The disclosure teaches the transdermal administration of phospholipid nanoparticle carrier composition of cannabinoids to deliver standardized and precision-metered dosages.

Intranasal Transport of Phospholipid Nanoparticle Cannabinoids Compositions Across the Nasal Cavity The disclosure teaches methods of the intranasal administration of phospholipid nanoparticle carrier compositions of cannabinoids across the membranes of the nasal cavity to increase the delivery, absorption and the bioavailability of cannabinoids into the blood stream and to target receptors of mammals.

The disclosure teaches intranasal administration of phospholipid nanoparticle carrier composition of cannabinoids across the membranes of the nasal cavity to increase the cannabinoids bioavailability; and/or the cannabinoids therapeutic activity and/or cannabinoids potencies in cannabinoid therapy.

The disclosure teaches intranasal administration of phospholipid nanoparticle carrier composition of cannabinoids across the membranes of the nasal cavity to increase the cannabinoids bioavailability, bioactivity, therapeutic activity and therapeutic index in cannabinoid therapy.

The disclosure teaches intranasal administration of phospholipid nanoparticle carrier composition of cannabinoids across the membranes of the nasal cavity to decrease the adverse effects of cannabinoid therapy.

The disclosure teaches intranasal administration of phospholipid nanoparticle carrier composition of cannabinoids across the membranes of the nasal cavity to decrease the adverse effects of cannabinoid therapy.

The disclosure teaches the transdermal administration of phospholipid nanoparticle carrier composition of cannabinoids to bypass GI track barriers and eliminate first pass liver metabolism effects with the inclusion of essential phospholipids in the nanoparticle's structural composition.

The disclosure teaches the transdermal administration of phospholipid nanoparticle carrier composition of cannabinoids to deliver standardized and precision-metered dosages.

The compositions of the invention may be administered to the nasal cavity in any suitable form, for example, in the form of drops or a spray. The preferred method is a NanoSphere liquid gel. Methods suitable for administering a composition to the nasal cavity will be well known by the person of ordinary skill in the art. Any suitable method may be used. The preferred method of administration is the use of a pump device.

Phospholipid Nanoparticle Cannabinoids Compositions for Intraoral Delivery Transport Across the Oral Mucosa The disclosure further teaches a method of administering and delivering lipid structured nanoparticles containing cannabinoids to the oral mucosa for transport into the systemic circulation by employing an intraoral phospholipid nanoparticle delivery system composition.

This disclosure teaches NanoSphere phospholipid nanoparticle compositions that are taken by sublingual administration. The liquid nanosphere gel is administered under the tongue for transport directly into the blood stream. Sublingual drug solutes are rapidly absorbed into the reticulated vein, which lies underneath the oral mucosa, and transported through the facial veins, internal jugular vein, andbraciocephalic vein and then drained in to systemic circulation.

EXAMPLES

Basic Intraoral Cannabinoid Phospholipid Nanoparticle Carrier Composition Formulation
25-75%—Cannabinoids
15-75%—Phospholipids (Lipoid Phospholipon 90 G, Lipoid Phospholipon 90 H, Lipoid Phospholipon 85 G, Lipoid S 75, Lipoid S 40, Lipoid S 80, Lipoid E 80, Lipoid Phosal 75 SA Lipoid, Lipoid Phosal 53 MCT)
25-75%—Lipids (medium chain triglycerides, glycerides, hemp seed oil, safflower oil, sunflower oil, etc.)
0-30%—Surfactants (lecithins such as Alcolec S, Alcolec BS and Alcolec XTRA-A, polysorbates such as Polysorbate 80 and Polysorbate 20, monoglycerides, diglycerides, triglycerides, glyceryl oleate, polaxamers)
0-10%—buffers (Sodium hydroxide)
20-60%—Solvents and Carrier Fluids (distilled water, glycerides, lipids)
0-5%—Preservatives (ascorbyl palmitate, rosemary oleoresin, tocopherol, potassium sorbate)
Basic Peroral Cannabinoid Phospholipid Nanoparticle Carrier Composition Formulation
15-75%—Cannabinoids
15-75%—Phospholipids (Lipoid Phospholipon 90 G, Lipoid Phospholipon 90 H, Lipoid Phospholipon 85 G, Lipoid S 75, Lipoid S 40, Lipoid S 80, Lipoid E 80, Lipoid Phosal 75 SA, Lipoid Phosal 53 MCT)
25-75%—Lipids (medium chain triglycerides, glycerides, hemp seed oil, safflower oil, sunflower oil, etc.)
0-40%—Surfactants (lecithins such as Alcolec S, Alcolec BS and Alcolec XTRA-A, polysorbates such as Polysorbate 80 and Polysorbate 20, monoglycerides, diglycerides, triglycerides, glyceryl oleate, polaxamers)
0-10%—buffers (Sodium hydroxide)
20-60%—Solvents and Carrier Fluids (distilled water, glycerdies, lipids)
0-5%—Preservatives (ascorbyl palmitate, rosemary oleoresin, tocopherol, potassium sorbate)
Basic Cannabinoid Transdermal Nanoparticle Carrier Composition in a Topical Gel Formulation
15-75%—Cannabinoids
5-30%—Phospholipids (Lipoid Phospholipon 90 G, Lipoid Phospholipon 90 H, Lipoid Phospholipon 85 G, Lipoid S 75, Lipoid E 80, Lipoid Phosal 75 SA, Lipoid Phosal 50 SA, Lipoid Phosal 53 MCT)
5-20%—Lipids (medium chain triglycerides, glycerides, hemp seed oil, safflower oil, sunflower oil, etc.)
5-50%—Penetration Enhancer (Ethanol)
0-40%—Surfactants (lecithins such as Alcolec S, Alcolec BS and Alcolec XTRA-A, polysorbates such as Polysorbate 80 and Polysorbate 20, monoglycerides, diglycerides, triglycerides, glyceryl oleate, polaxamers)
1-3%—Gelling Agent (Xanthum Gum, Carbopol)
0.1-1%—Preservatives (Optiphen, Jeecide Potassium Sorbate)
q.s.—Carrier (distilled water)
0-5%—Preservatives (Polyquaternium-1, benzalkonium chloride)

Basic Cannabinoid Intransal Nanoparticle Carrier Composition
5-40%—Cannabinoids
5-35%—Phospholipids (Lipoid Phospholipon 90 G, Lipoid Phospholipon 90 H, Lipoid Phospholipon 85 G, Lipoid S 75, Lipoid E 80, etc.)
2-15%—Lipids (medium chain triglycerides, glycerides, hemp seed oil, safflower oil, sunflower oil, etc.)
0-40% Surfactants (lecithins such as Alcolec S, Alcolec BS and Alcolec XTRA-A, polysorbates such as Polysorbate 80 and Polysorbate 20, monoglycerides, diglycerides, triglycerides, glyceryl oleate, polaxamers)
0.5-2.5%—Buffers (monobasic potassium phosphate, dibasic potassium phosphate)
0.6-1.8%—Tonicity Adjustor (Sodium chloride)
0-0.25%—Chelating Agents (EDTA)
0.01-0.05%—Preservatives (Benzalkonium chloride)
q.s.—Carrier (distilled water, lipids)

Example 1

Procedure for a 20:1 CBD to THC Cannabinoid Phospholipid Nanoparticle Carrier Composition for Intraoral Delivery Completely dissolve 2285 mg of phospholipids (Lipoid Phospholipon 85 G) into 3800 mg of Hempseed Oil in a vessel under low heat and stirring at low RPM. Next, discharge 2000 mg of 95% purified 20:1 CBD (cannabidiol) to THC (tetrahydrocannabinol) cannabis sativa extract into the blend. In sequence, pre-nanoparticle blend is ground through a product mill for particle size reduction, at 10,000 RPM for 10 minutes with an Ultra-Turrax homogenizer under cooling, and processed in an ultrasonification system for 35 minutes with 3000 watts of power in a flow through chamber under cooling to form the phospholipid nanoparticle cannabinoid composition. Next, 20 mg of potassium sorbate preservative, 150 mg of flavor oil and 50 mg of steviol glycoside sweetener is thoroughly dispersed into the composition.

The weight concentration of CBD+THC in the phospholipid nanoparticle cannabinoid carrier composition is 25%. Composition is administered to the sublingual mucosa by a precision liquid pump device bottle that delivers 125 mcl per pump. Each pump dose contains 30 mg of CBD and 1.5 mg of THC as a phospholipid nanoparticle delivered intra-orally into the systemic circulation with increased bioavailability, therapeutic activity and therapeutic index.

Example 2

Procedure for a 20:1 CBD to THC Cannabinoid Phospholipid Nanoparticle Gel Composition for Transdermal Delivery Completely dissolve 2595 of phospholipids (Lipoid Phospholipon 85 G, 2525 mg of 95% purified 20:1 CBD (cannabidiol) to THC (delta-9-tetrahydrocannabinol, 1450 mg of medium chain triglycerides and 1635 mg of polysorbate 80 is into a closed vessel containing 6535 mg of ethanol stirring at 1250 RPM. Heat this vessel to 300 C. Next, discharge 900 mg of water heated to 300 C into the vessel from a separate heated vessel. Stir this vessel containing pre-nanoparticle blend for 5 minutes. In sequence, pre-nanoparticle blend is ground through a product mill for particle size reduction, homogenate at 10,000 RPM for 10 minutes with a Ultra-Turrax homogenizer under cooling, and processed in an ultrasonification system for 40 minutes with 3000 watts of power in a flow through chamber under cooling to form the phospholipid nanoparticle cannabinoid composition. Discharge 3425 mg of ethanol into a vessel containing the blend stirring at 1250 RPM. Next discharge 250 mg of Xanthum gum into a vessel containing the blend stirring at 1250 RPM. Follow by discharging 33 mg of potassium sorbate preservative in the vessel and stir for 5 minutes.

The weight concentration of CBD+THC in the phospholipid nanoparticle carrier composition is 20%. The NanoSphere Gel composition is administered topically to skin by precision liquid pump device bottle that delivers 250 mcl per pump. Each pump contains 50 mg of CPD and 2.5 mg of THC as cannabinoid phospholipid nanoparticles delivered transdermally into the systemic circulation with increased bioavailability, therapeutic activity and therapeutic index Example 3

Procedure for a 1:1 THC to CBD Cannabinoid Phospholipid Nanoparticle Carrier Composition for Intranasal Delivery Completely dissolve 2285 mg of phospholipids (Lipoid Phospholipon 85 G) into 3800 mg of medium chain triglycerides in a vessel under low heat and stirring at low RPM. Next, discharge 1300 mg of 95% purified 1:1 THC (delta-9-tetrahydrocannabinol) to CBD (cannabidiol) cannabis sativa extract into the blend. Follow by discharging 1280 mg of polysorbate 80 into the blend. In sequence, pre-nanoparticle blend is ground through a product mill for particle size reduction, homogenate at 10,000 RPM for 10 minutes with an Ultra-Turrax homogenizer under cooling, and processed in an ultrasonification system for 35 minutes with 3000 watts of power in a flow through chamber under cooling to form the phospholipid nanoparticle cannabinoid composition. Next discharge 1346 mg of distilled water and 4 mg of ethanol into phospholipid nanoparticle cannabinoid composition while stirring at 10,000 RPM for 10 minutes. Next discharge 35 mg monobasic potassium phosphate and 34 mg of dibasic potassium phosphate in to the composition while stirring at 2500 rpm. Follow by discharging 75 mg of sodium chloride, 30 mg of EDTA sodium and 1.5 mg of benzalkonium chloride preservative into the composition while stirring.

The weight concentration of THC+CBD in the phospholipid nanoparticle cannabinoid carrier composition is 20%. Composition is administered to nasal mucosa by precision liquid pump device bottle that delivers 75 mcl per pump. Each pump dose contains 7.5 mg of THC and 7.5 mg of CBD as a phospholipid nanoparticle delivered intra-orally into the systemic circulation with increased bioavailability, therapeutic activity and therapeutic index.

Example 4

Procedure for 30 mg of CBD and 1.5 mg of THC Cannabinoids in Phospholipid Nanoparticles for Intraoral Delivery Completely disperse 1,3396.37 gm of phospholipids (Lipoid Phospholipon 85 G), with 1,6425.50 gm of medium chain triglycerides in a closed vessel stirring at 1500 RPM and heated 45° C. Disperse 1,467.42 gm of 95% purified CBD full spectrum cannabis oil extract supplying 20:1 CBD (cannabidiol) to THC (delta-9-tetrahydrocannabinol) in the heated vessel. Disperse 38.25 gm of soya lecithin (Alcolec LPC 20) and 607 gm polysorbate 80 into the vessel followed by 2475 gm of water into the vessel. Stir until completely dispersed.

In sequence process pre-nanoparticle blend through an ointment mill, homogenate at 10,000 RPM for 10 minutes with an Ultra-Turrax at 45° C., and process with ultrasonification for 30 minutes with 3000 watts of power in a flow through chamber under cooling to form a phospholipid nanoparticle cannabinoid viscoelastic gel composition. Next, 16.2 gm of potassium sorbate preservative 22.5 gm steviol glycoside sweetener and 67 gm of natural flavor is thoroughly dispersed into the phospholipid lipid nanoparticle composition.

The weight concentration of cannabinoids encapsulated in the NanoSphere phospholipid nanoparticle composition for CBD and THC are 17.32%. and 87%. The dosage is 175 mcl. The NanoSphere gel composition is administered to the sublingual mucosa by a precision liquid pump device bottle that delivers 175 mcl per pump. Each pump intraorally delivers a standardized precision-metered dose of 30 mg of CBD and 1.5 mg of THC of a full spectrum cannabis high CBD extract encapsulated in Nanosphere phospholipid nanoparticle viscoelstic gel into the systemic circulation.

Example 5

Procedure for 35 mg of CBD of Hempseed Oil Cannabinoid Extract in Phospholipid Nanoparticles for Intraoral Delivery Completely disperse 1,291.95 gm of phospholipids (Lipoid Phospholipon 85 G), with 3,786.75 gm of 42% CBD hempseed oil extract in a closed vessel stirring at 1500 RPM and heated to 45° C. Disperse 35.20 gm of soya lecithin (Alcolec LPC 20) and 601.42 gm of polysorbate 80 into the vessel followed by 2227.5 gm of water into the vessel. Stir until completely dispersed.

In sequence process pre-nanoparticle blend through an ointment mill, homogenate at 10,000 RPM for 10 minutes with an Ultra-Turrax at 45° C. and process with ultrasonification for 30 minutes with 3000 watts of power in a flow through chamber under cooling to form a phospholipid nanoparticle cannabinoid viscoelastic gel composition. Next, 14.48 gm of potassium sorbate preservative and 22.27 gm steviol glycoside sweetener is thoroughly dispersed into the phospholipid lipid nanoparticle composition.

The weight concentration encapsulated in the NanoSphere phospholipid nanoparticle composition for CBD is 19.9%. The he dosage is 175 mcl. The Nanosphere gel composition is administered to the sublingual mucosa by a precision liquid pump device bottle that delivers 175 mcl per pump. Each pump intraorally delivers a standardized precision-metered dose of 35 mg of CBD from a 42% CBD hempseed oil extract encapsulated in NanoSphere phospholipid nanoparticle viscoelstic gel into the systemic circulation.

Example 6

Procedure for 25 mg THC and 5 mg CBD Cannabis Oil Cannabinoid Extract in Phospholipid Nanoparticles for Intraoral Delivery Completely disperse 1,125 gm of phospholipids (Lipoid Phospholipon 85 G, with 990.2 gm of medium chain triglycerides in a closed vessel stirring at 1500 RPM and heated 45° C. Disperse 1,401 gm of full spectrum butane cannabis oil extract supplying 47.32% THC (delta-9-tetrahydrocannabinol). 9.52% CBD and 3.82% CBN into the heated vessel. Disperse 38.25 gm of soya lecithin (Alcolec LPC 20) and 652.5 gm polysorbate 80 followed by 2430 gm of water into the vessel. Stir until completely dispersed.

In sequence process pre-nanoparticle blend through an ointment mill, homogenate at 10,000 RPM for 10 minutes with an Ultra-Turrax at 45° C., and process with ultrasonification for 30 minutes with 3000 watts of power in a flow through chamber under cooling to form a phospholipid nanoparticle cannabinoid viscoelastic gel composition. Next, 16.2 gm of potassium sorbate preservative 20.15 gm steviol glycoside sweetener and 60 gm of natural flavor is thoroughly dispersed into the phospholipid lipid nanoparticle composition.

The weight concentration of cannabinoids encapsulated in the NanoSphere phospholipid nanoparticle composition for THC, CBD and CBN are 14.29%, 2.88%, and 2.88%. The dosage is 175 mcl. The Nanosphere gel composition is administered to the sublingual mucosa by a precision liquid pump device bottle that delivers 175 mcl per pump. Each pump intraorally delivers a standardized precision-metered dose of 25 mg of THC and 1.5 mg of CBD of a full spectrum cannabis butane extract encapsulated in NanoSphere phospholipid nanoparticle viscoelastic gel into the systemic circulation.

Example 7

Procedure for 7.5 mg of THC and 7.5 mg of CBD Cannabinoids in Phospholipid Nanoparticle for Intranasal Delivery Completely disperse 690 gm of phospholipids (Lipoid Phospholipon 85 G) with 390 gm of medium chain triglycerides in a closed vessel stirring at 1500 RPM and heated 45° C. Disperse 1,401 gm of a full spectrum CO2 cannabis oil extract supplying 32.25% THC (delta-9-tetrahydrocannabinol) and 32.25. CBD into the heated vessel. Disperse 24 gm of soya lecithin (Alcolec LPH 20) and 240.2 gm polysorbate 80 followed by 1,650 gm of water into the vessel. Stir until completely dispersed.

In sequence process pre-nanoparticle blend through an ointment mill, homogenate at 10,000 RPM for 10 minutes with an Ultra-Turrax at 45° C., and process in an ultrasonification for 30 minutes with 3000 watts of power in a flow through chamber under cooling to forma phospholipid nanoparticle cannabinoid viscoelastic gel composition. Next discharge 16.8 of EDTA sodium, 10.5 gm of monobasic potassium phosphate and 11.4 gm of dibasic sodium phosphate in to the composition while stirring at 2500 rpm.

The weight concentration of THC+CBD in the phospholipid nanoparticle cannabinoid carrier composition is 12%. The dosage is 125 mcl. The NanoSphere Gel composition is administered to nasal mucosa by precision liquid pump device bottle that delivers 125 mcl per pump. Each pump delivers a standardized precision-metered dose of 7.5 mg of THC and 7.5 mg of CBD encapsulated in NanoSphere phospholipid nanoparticle gel intranasal delivered into the systemic circulation.

Example 8

Procedure for 50 mg of CBD and 2.5 mg of THC Cannabinoids in Phospholipid Nanoparticle for Transdermal Delivery Completely disperse 1,755 gm of phospholipids (Lipoid Phospholipon 85 G, with 1,170 gm of medium chain triglycerides in a closed vessel stirring at 1500 RPM and heated 45° C. Disperse 2,387.36 gm of 95% purified CBD full spectrum cannabis oil extract supplying 20:1 CBD (cannabidiol) to THC (delta-9-tetrahydrocannabinol, in the heated vessel. Disperse 990 gm polysorbate 80 into the vessel followed by 2,475 gm of water mixed with 2,272.5 gm of ethanol into the vessel. Stir until completely dispersed.

In sequence process pre-nanoparticle blend through an ointment mill, homogenate at 10,000 RPM for 10 minutes with an Ultra-Turrax at 45° C., and process in an ultrasonification for 30 minutes with 3000 watts of power in a flow through chamber under cooling to forma phospholipid nanoparticle cannabinoid viscoelastic gel composition. Next discharge 202.5 gm of xanthum gum into a vessel containing the blend stirring at 1500 RPM. Follow by discharging 22.5 gm of potassium sorbate preservative in the vessel and stir for 5 minutes.

The weight concentration of CBD+THC in the phospholipid nanoparticle carrier composition is 21%. The dosage is 250 mcl. The NanoSphere Gel composition is administered topically to skin by precision liquid pump device bottle that delivers 250 mcl per pump. Each pump delivers a standardized precision-metered dose of 50 mg of CBD and 2.5 mg of THC of a full spectrum high CBD cannabis extract encapsulated in NanoSphere phospholipid nanoparticle viscoelstic gel transdermally delivered into the systemic circulation.

While the apparatus and method have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

While the method and agent have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

It should also be understood that a variety of changes may be made without departing from the essence of the disclosure. Such changes are also implicitly included in the description. They still fall within the scope of this disclosure. It should be understood that this disclosure is intended to yield a patent covering numerous aspects of the disclosure both independently and as an overall system and in both method and apparatus modes. Further, each of the various elements of the disclosure and claims may also be achieved in a variety of manners. This disclosure should be understood to encompass each such variation, be it a variation of an embodiment of any apparatus embodiment, a method or process embodiment, or even merely a variation of any element of these.

Particularly, it should be understood that as the disclosure relates to elements of the disclosure, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this disclosure is entitled.

It should be understood that all actions may be expressed as a means for taking that action or as an element which causes that action.

Similarly, each physical element disclosed should be understood to encompass a disclosure of the action, which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Finally, all referenced listed in the Information Disclosure Statement or other information statement filed with the application are hereby appended and hereby incorporated by reference; however, as to each of the above, to the extent that such information or statements incorporated by reference might be considered inconsistent with the patenting of this/these disclosure(s), such statements are expressly not to be considered as made by the applicant(s).

In this regard, it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

The description of the present invention has been presented for purposes of illustration and description, but is not intended to be exhaustive or limiting of the invention to the form disclosed. The scope of the present invention is limited only by the scope of the following claims. Many modifications and variations will be apparent to those of ordinary skill in the art. The embodiment described and shown in the figures was chosen and described in order to best explain the principles of the invention, the practical application, and to enable others of ordinary skill in the art to understand the invention for various embodiments with various modifications as are suited to the particular use contemplated.

The invention claimed is:

1. A drug delivery system comprising nanoparticle structures;
   wherein a single layer of essential phospholipids encapsulates liquid lipids and cannabinoids in each nanoparticle structure; wherein the phospholipid content (weight/volume) of the nanoparticle structures is 5-30%;
   wherein the nanoparticle structures have a particle size distribution from 50 to 150 nm; and
   wherein the nanoparticle structures yield standardized precision-metered dose cannabinoids.

2. The drug delivery system of claim 1, wherein the essential phospholipids are comprised of greater than 85% phosphatidylcholine.

3. The drug delivery system of claim 1, wherein the nanoparticle structures do not contain surfactants.

4. The drug delivery system of claim 1, wherein the nanoparticle structures can be administered via the sublingual mucosa and buccal mucosa of a mammal.

5. The drug delivery system of claim 1, wherein the nanoparticle structures can be administered across dermal and epidermal barriers.

6. The drug delivery system of claim 1, wherein the nanoparticle structures can be administered across nasal mucosal barriers.

7. The drug delivery system of claim 1, wherein the nanoparticle structures can be administered across the intestinal mucosal barriers.

8. The drug delivery system of claim 1, wherein the nanoparticle structures are composed of an outer phospholipid membrane and adjustable viscoelastic gel lipid core.

9. The drug delivery system of claim 1; wherein the nanoparticle increases the bioavailability of the cannabinoid 2-fold to 8-fold compared to bioavailability without nanoparticle encapsulation.

10. The drug delivery system of claim 1; wherein the nanoparticle structures decrease the dose of cannabinoids 2-fold to 8-fold less than an amount of cannabinoids needed to elicit the same therapeutic effect compared to raw and non-encapsulated cannabinoids in a patient in need thereof.

11. The drug delivery system of claim 1; wherein the nanoparticle structures reduce the adverse effects of cannabinoids compared to adverse effects of cannabinoids without nanoparticle encapsulation.

12. A method of cannabinoid therapy comprising administering to a mammal a phospholipid nanoparticle structure; wherein cannabinoids are encapsulated in the nanoparticle structure; wherein a single layer of essential phospholipids encapsulates liquid lipids and the cannabinoids in the nanoparticle structure; wherein the phospholipid content (weight/volume) of the nanoparticle structure is 5-30%; wherein the nanoparticle structure has a particle size distribution from 50 to 150 nm; wherein the nanoparticle structure yields standardized precision-metered dose cannabinoids.

13. The method of claim 12 wherein the therapeutic activity of cannabinoids is increased; and wherein cannabinoid adverse effects are reduced.

* * * * *